US008268620B2

(12) United States Patent
Thomson et al.

(10) Patent No.: US 8,268,620 B2
(45) Date of Patent: Sep. 18, 2012

(54) OCT4 AND SOX2 WITH SV40 T ANTIGEN PRODUCE PLURIPOTENT STEM CELLS FROM PRIMATE SOMATIC CELLS

(75) Inventors: James Thomson, Madison, WI (US); Junying Yu, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 48 days.

(21) Appl. No.: 12/605,220

(22) Filed: Oct. 23, 2009

(65) Prior Publication Data

US 2010/0184227 A1 Jul. 22, 2010

Related U.S. Application Data

(60) Provisional application No. 61/108,362, filed on Oct. 24, 2008.

(51) Int. Cl.
*C12N 15/00* (2006.01)
(52) U.S. Cl. .................. 435/377; 435/373; 435/383
(58) Field of Classification Search .................. None
See application file for complete search history.

(56) References Cited

U.S. PATENT DOCUMENTS

| 2009/0047263 A1* | 2/2009 | Yamanaka et al. | 424/93.21 |
| 2009/0191159 A1* | 7/2009 | Sakurada et al. | 424/93.7 |
| 2010/0003757 A1* | 1/2010 | Mack et al. | 435/455 |

FOREIGN PATENT DOCUMENTS

| WO | 2009133971 A1 | 11/2009 |
| WO | 2009149233 A1 | 12/2009 |
| WO | 2010012077 A1 | 2/2010 |

OTHER PUBLICATIONS

Cowan et al. Nuclear Reprogramming of Somatic Cells After Fusion with Human Embryonic Stem Cells.Science, 2005, vol. 309, pp. 1369-1373.*
Jha et al. Sv40 Mediated Immortalization. Experimental Cell Res., 1998, vol. 245, pp. 1-7.*
Mali et al. Improved Efficiency and Pace of Generating Induced Pluripotent Stem Cells from Human Adult and Fetal Fibroblasts. Stem Cells, 2008, vol. 26, pp. 1998-2005.*
Carey B W et al: Reprogramming of murine and human somatic cells using a single polycistronic vector, Proceedings of the National Academy of Sciences of the United States of America, Jan. 6, 2009, pp. 157-162, vol. 106, No. 1.
Conese M et al: Gene therapy progress and prospects: Episomally maintained self-replicating systems, Gene Therapy, Dec. 2004, pp. 1735-1741, vol. 11, No. 24.
Okita Keisuke et al: Generation of mouse induced pluripotent stem cells without viral vectors, Science, Oct. 9, 2008, pp. 949-953, vol. 322, No. 5903, Washington DC.
Yu Junying et al: Induced pluripotent stem cell lines derived from human somatic cells, Science, American Association for the Advancement of Science, US, Dec. 21, 2007, pp. 1917-1920, vol. 318, No. 5858.
Yu Junying et al: Human induced pluripotent stem cells free of vector and transgene sequences, Science, May 8, 2009, pp. 797-801, vol. 324, No. 5928, New York, NY.
Kabouridis, PS, "Biological applications of the protein transduction technology." Trends in Biotechnology, 21:498-503 (2003).

\* cited by examiner

*Primary Examiner* — Deborah Crouch
(74) *Attorney, Agent, or Firm* — Quarles & Brady LLP

(57) ABSTRACT

Methods for reprogramming primate somatic cells to pluripotency using an episomal vector that does not encode an infectious virus are disclosed. Pluripotent cells produced in the methods are also disclosed.

16 Claims, 6 Drawing Sheets

Fig. 1A
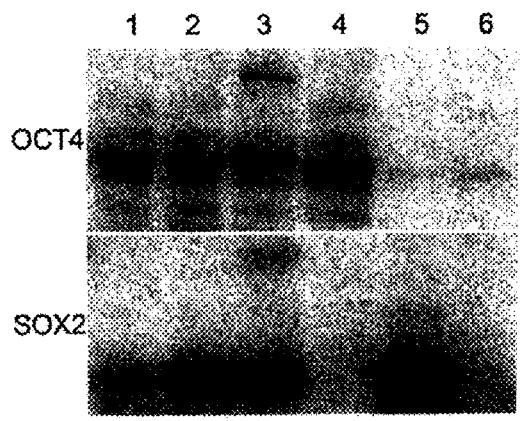
Fig. 1B
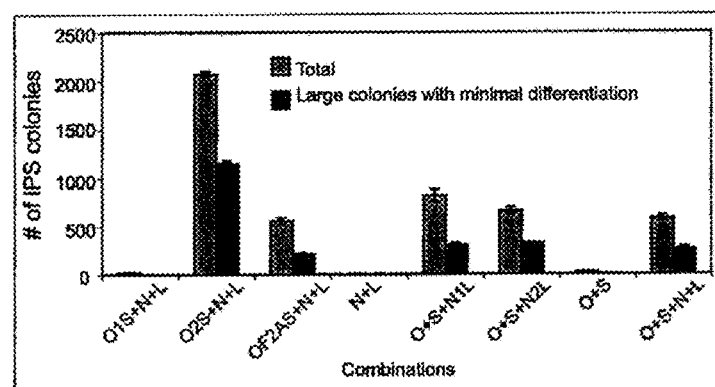
FIGURE 1

Fig. 2A
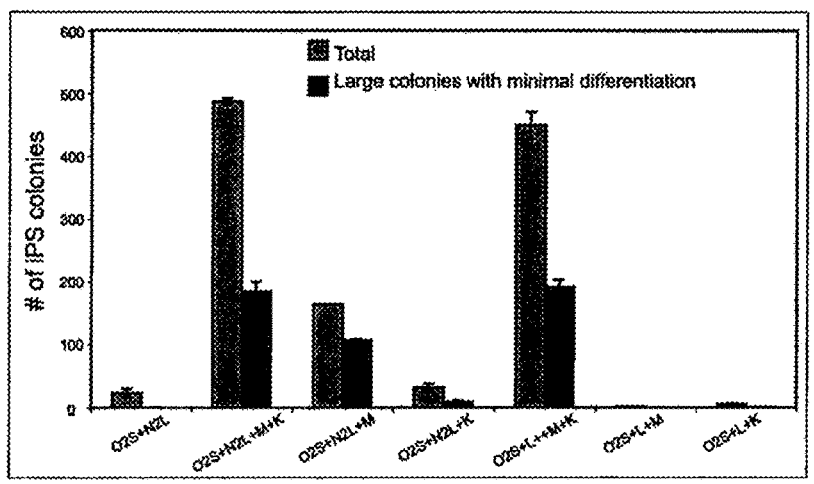
Fig. 2B
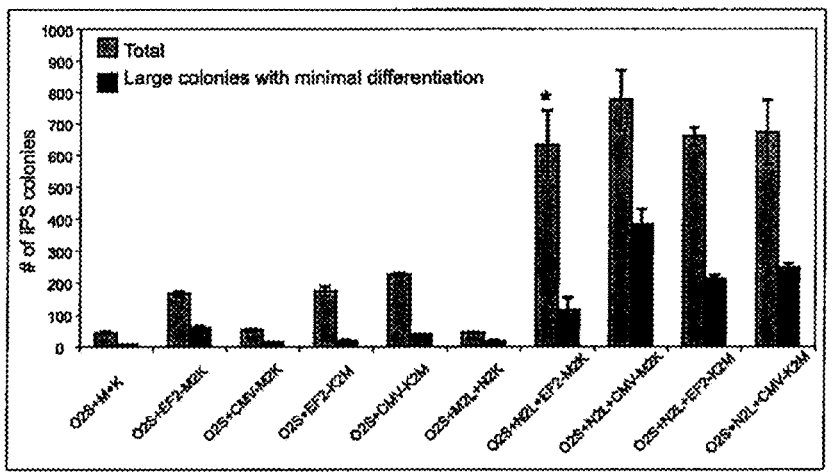
Fig. 2C
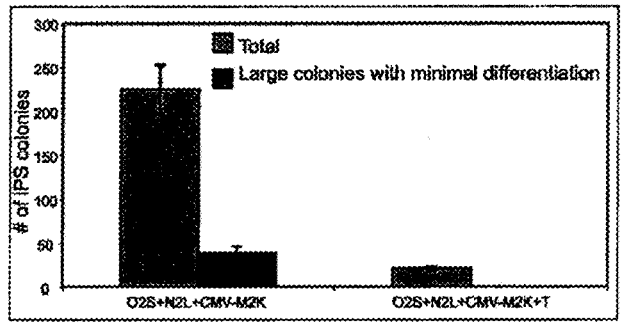
FIGURE 2

Fig. 3A
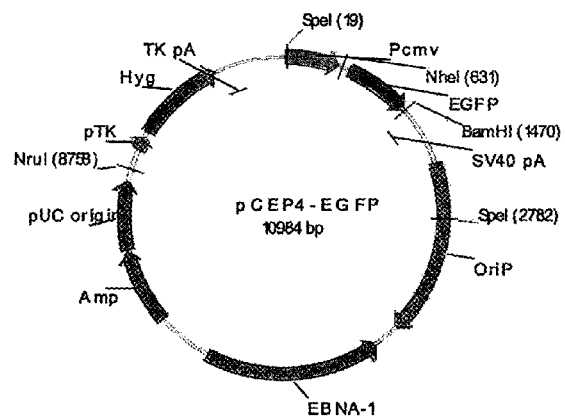
Fig. 3B
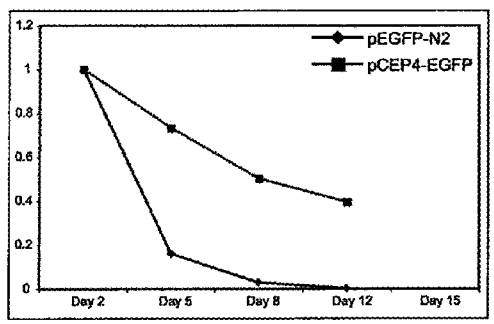
FIGURE 3

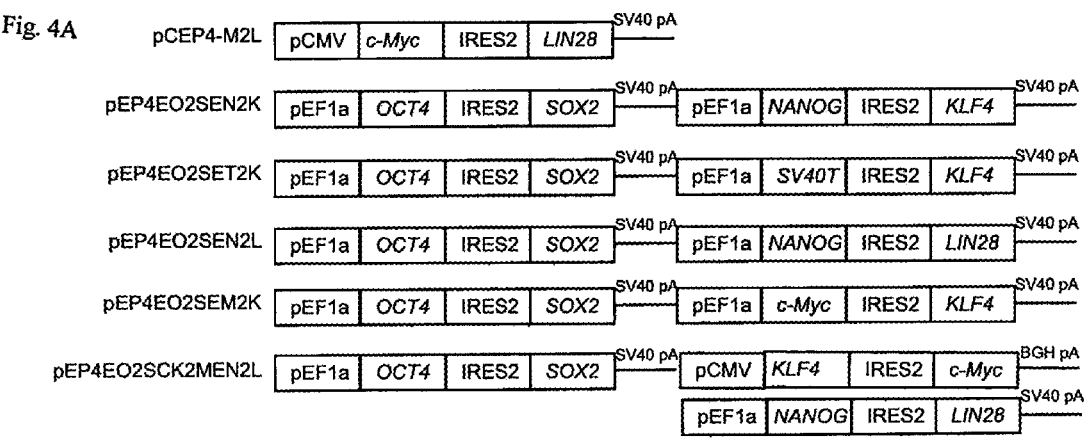
Fig. 4A
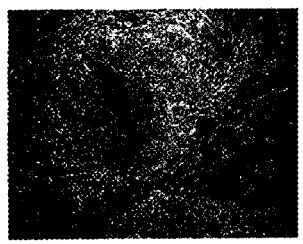
Fig. 4B
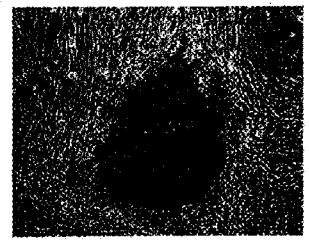
Fig. 4C
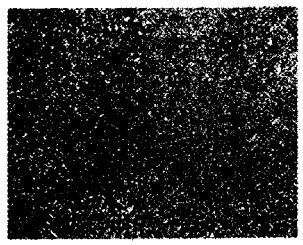
Fig. 4D
FIGURE 4

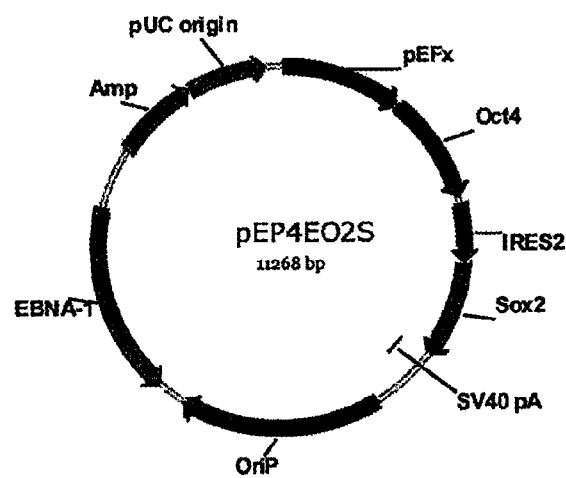
Fig. 5A
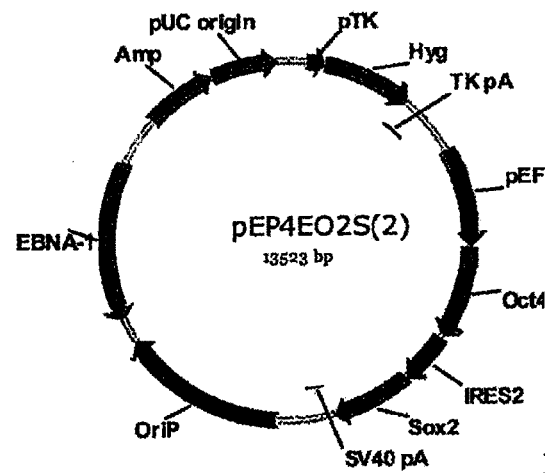
Fig. 5B
FIGURE 5

SEQUENCE LISTING

<160> NUMBER OF SEQ ID NOS: 12

<210> SEQ ID NO 1
<211> LENGTH: 1411
<212> TYPE: DNA
<213> ORGANISM: Homo sapiens

<400> SEQUENCE: 1

```
ccttcgcaag ccctcatttc accaggcccc cggcttgggg cgccttcctt ccccatggcg        60
ggacacctgg cttcggattt cgccttctcg cccctccag gtggtggagg tgatgggcca       120
ggggggccgg agccgggctg ggttgatcct cggacctggc taagcttcca aggccctcct       180
ggagggccag gaatcgggcc gggggttggg ccaggctctg aggtgtgggg gattccccca       240
tgcccccgc cgtatgagtt ctgtgggggg atggcgtact gtgggcccca ggttggagtg        300
gggctagtgc cccaaggcgg cttggagacc tctcagcctg agggcgaagc aggagtcggg       360
gtggagagca actccgatgg ggcctccccg gagccctgca ccgtcacccc tggtgccgtg       420
aagctggaga aggagaagct ggagcaaaac ccggaggagt cccaggacat caaagctctg       480
cagaaagaac tcgagcaatt tgccaagctc ctgaagcaga gaggatcac cctgggatat       540
acacaggccg atgtgggggct caccctgggg gttctatttg gaaggtatt cagccaaacg       600
accatctgcc gctttgaggc tctgcagctt agcttcaaga acatgtgtaa gctgcggccc       660
ttgctgcaga agtgggtgga ggaagctgac aacaatgaaa atcttcagga gatatgcaaa       720
gcagaaaccc tcgtgcaggc ccgaaagaga aagcgaacca gtatcgagaa ccgagtgaga       780
ggcaacctgg agaatttgtt cctgcagtgc ccgaaaccca cactgcagca gatcagccac       840
atcgcccagc agcttgggct cgagaaggat gtggtccgag tgtggttctg taaccggcgc       900
cagaagggca gcgatcaag cagcgactat gcacaacgag aggattttga ggctgctggg       960
tctcctttct caggggggacc agtgtccttt cctctgcccc cagggcccca tttttggtacc      1020
ccaggctatg ggagccctca cttcactgca ctgtactcct cggtccctt ccctgagggg       1080
gaagcctttc ccctgtctc cgtcaccact ctgggctctc ccatgcattc aaactgaggt       1140
gcctgccctt ctaggaatgg gggacagggg gagggagga gctagggaaa gaaaacctgg       1200
agtttgtgcc agggtttttg ggattaagtt cttcattcac taaggaagga attgggaaca       1260
caaagggtgg gggcagggga gtttggggca actggttgga gggaaggtga agttcaatga      1320
tgctcttgat tttaatccca catcatgtat cacttttttc ttaaataaag aagcctggga       1380
cacagtagat agacacactt aaaaaaaaaa a                                      1411
```

<210> SEQ ID NO 2
<211> LENGTH: 2518
<212> TYPE: DNA
<213> ORGANISM: Homo sapiens

<400> SEQUENCE: 2

| | | | | | |
|---|---|---|---|---|---|
| ctattaactt | gttcaaaaaa | gtatcaggag | ttgtcaaggc | agagaagaga | gtgtttgcaa     60 |
| aaggggggaaa | gtagtttgct | gcctctttaa | gactaggact | gagagaaaga | agaggagaga    120 |
| gaaagaaagg | gagagaagtt | tgagcccag | gcttaagcct | ttccaaaaaa | taataataac    180 |
| aatcatcggc | ggcggcagga | tcggccagag | gaggagggaa | gcgctttttt | tgatcctgat    240 |
| tccagtttgc | ctctctcttt | ttttccccca | aattattctt | cgcctgattt | tcctcgcgga    300 |
| gccctgcgct | cccgacaccc | ccgcccgcct | ccctcctcc | tctcccccg | cccgcgggcc    360 |
| ccccaaagtc | ccggccgggc | cgaggtcgg | cggccgccgg | cgggccgggc | ccgcgcacag    420 |
| cgcccgcatg | tacaacatga | tggagacgga | gctgaagccg | ccgggcccgc | agcaaacttc    480 |
| ggggggcggc | ggcggcaact | ccaccgcggc | ggcggccggc | ggcaaccaga | aaaacagccc    540 |
| ggaccgcgtc | aagcggccca | tgaatgcctt | catggtgtgg | tcccgcgggc | agcggcgcaa    600 |
| gatggcccag | gagaacccca | agatgcacaa | ctcggagatc | agcaagcgcc | tgggcgccga    660 |
| gtggaaactt | ttgtcggaga | cggagaagcg | gccgttcatc | gacgaggcta | gcggctgcg    720 |
| agcgctgcac | atgaaggagc | acccggatta | taaataccgg | ccccggcgga | aaaccaagac    780 |
| gctcatgaag | aaggataagt | acacgctgcc | cggcgggctg | ctggccccg | gcggcaatag    840 |
| catggcgagc | ggggtcgggg | tgggcgccgg | cctgggcgcg | ggcgtgaacc | agcgcatgga    900 |
| cagttacgcg | cacatgaacg | gctggagcaa | cggcagctac | agcatgatgc | aggaccagct    960 |
| gggctacccg | cagcacccgg | gcctcaatgc | gcacggcgca | gcgcagatgc | agcccatgca   1020 |
| ccgctacgac | gtgagcgccc | tgcagtacaa | ctccatgacc | agctcgcaga | cctacatgaa   1080 |
| cggctcgccc | acctacagca | tgtcctactc | gcagcagggc | acccctggca | tggctcttgg   1140 |
| ctccatgggt | tcggtggtca | agtccgaggc | cagctccagc | cccccgtgtg | gttacctcttc   1200 |
| ctcccactcc | agggcgccct | gccaggccgg | ggacctccgg | gacatgatca | gcatgtatct   1260 |
| ccccggcgcc | gaggtgccgg | aacccgccgc | ccccagcaga | cttcacatgt | cccagcacta   1320 |
| ccagagcggc | ccggtgcccg | gcacggccat | taacggcaca | ctgccctct | cacacatgtg   1380 |
| agggccggac | agcgaactgg | agggggggaga | aattttcaaa | gaaaacgag | ggaaatggga   1440 |
| ggggtgcaaa | agaggagagt | aagaaacagc | atggagaaaa | cccggtacgc | tcaaaaagaa   1500 |
| aaaggaaaaa | aaaaaatccc | atcacccaca | gcaaatgaca | gctgcaaaag | agaacaccaa   1560 |
| tcccatccac | actcacgcaa | aaaccgcgat | gccgacaaga | aaacttttat | gagagagatc   1620 |
| ctggacttct | ttttgggggga | ctattttttgt | acagagaaaa | cctggggagg | gtggggaggg   1680 |
| cgggggaatg | gaccttgtat | agatctggag | gaaagaaagc | tacgaaaaac | ttttttaaaag   1740 |
| ttctagtggt | acggtaggag | ctttgcagga | agtttgcaaa | agtctttacc | aataatattt   1800 |
| agagctagtc | tccaagcgac | gaaaaaaatg | ttttaatatt | tgcaagcaac | ttttgtacag   1860 |
| tatttatcga | gataaacatg | gcaatcaaaa | tgtccattgt | ttataagctg | agaatttgcc   1920 |
| aatattttttc | aaggagaggc | ttcttgctga | attttgattc | tgcagctgaa | atttaggaca   1980 |
| gttgcaaacg | tgaaaagaag | aaaattattc | aaatttggac | attttaattg | tttaaaaatt   2040 |
| gtacaaaagg | aaaaaattag | aataagtact | ggcgaaccat | ctctgtggtc | ttgtttaaaa   2100 |
| agggcaaaag | ttttagactg | tactaaattt | tataacttac | tgttaaaagc | aaaaatggcc   2160 |

| | | | | |
|---|---|---|---|---|
| atgcaggttg | acaccgttgg | taatttataa | tagcttttgt | tcgatcccaa ctttccattt | 2220 |
| tgttcagata | aaaaaaacca | tgaaattact | gtgtttgaaa | tattttctta tggtttgtaa | 2280 |
| tatttctgta | aatttattgt | gatattttaa | ggttttcccc | cctttatttt ccgtagttgt | 2340 |
| attttaaaag | attcggctct | gtattatttg | aatcagtctg | ccgagaatcc atgtatatat | 2400 |
| ttgaactaat | atcatcctta | taacaggtac | attttcaact | taagttttta ctccattatg | 2460 |
| cacagtttga | gataaataaa | ttttgaaat | atggacactg | aaaaaaaaaa aaaaaaa | 2518 |

```
<210> SEQ ID NO 3
<211> LENGTH: 2098
<212> TYPE: DNA
<213> ORGANISM: Homo sapiens

<400> SEQUENCE: 3
```

| | | | | | |
|---|---|---|---|---|---|
| attataaatc | tagagactcc | aggattttaa | cgttctgctg | gactgagctg gttgcctcat | 60 |
| gttattatgc | aggcaactca | ctttatccca | atttcttgat | acttttcctt ctggaggtcc | 120 |
| tatttctcta | acatcttcca | gaaaagtctt | aaagctgcct | taaccttttt tccagtccac | 180 |
| ctcttaaatt | ttttcctcct | cttcctctat | actaacatga | gtgtggatcc agcttgtccc | 240 |
| caaagcttgc | cttgctttga | agcatccgac | tgtaaagaat | cttcacctat gcctgtgatt | 300 |
| tgtgggcctg | aagaaaacta | tccatccttg | caaatgtctt | ctgctgagat gcctcacacg | 360 |
| gagactgtct | ctcctcttcc | ttcctccatg | gatctgctta | ttcaggacag ccctgattct | 420 |
| tccaccagtc | ccaaaggcaa | acaacccact | tctgcagaga | gagtgtcgc aaaaaaggaa | 480 |
| gacaaggtcc | cggtcaagaa | acagaagacc | agaactgtgt | tctcttccac ccagctgtgt | 540 |
| gtactcaatg | atagatttca | gagacagaaa | tacctcagcc | tccagcagat gcaagaactc | 600 |
| tccaacatcc | tgaacctcag | ctacaaacag | gtgaagacct | ggttccagaa ccagagaatg | 660 |
| aaatctaaga | ggtggcagaa | aaacaactgg | ccgaagaata | gcaatggtgt gacgcagaag | 720 |
| gcctcagcac | ctacctaccc | cagcctttac | tcttcctacc | accagggatg cctggtgaac | 780 |
| ccgactggga | accttccaat | gtggagcaac | cagacctgga | caattcaac ctggagcaac | 840 |
| cagacccaga | acatccagtc | ctggagcaac | cactcctgga | acactcagac ctggtgcacc | 900 |
| caatcctgga | caatcaggc | ctggaacagt | cccttctata | actgtggaga ggaatctctg | 960 |
| cagtcctgca | tgcagttcca | gccaaattct | cctgccagtg | acttggaggc tgccttggaa | 1020 |
| gctgctgggg | aaggccttaa | tgtaatacag | cagaccacta | ggtattttag tactccacaa | 1080 |
| accatggatt | tattcctaaa | ctactccatg | aacatgcaac | ctgaagacgt gtgaagatga | 1140 |
| gtgaaactga | tattactcaa | tttcagtctg | gacactggct | gaatccttcc tctcccctcc | 1200 |
| tcccatccct | cataggattt | tcttgtttg | gaaaccacgt | gttctggttt ccatgatgcc | 1260 |
| catccagtca | atctcatgga | gggtggagta | tggttggagc | ctaatcagcg aggtttcttt | 1320 |
| ttttttttt | ttcctattgg | atcttcctgg | agaaaatact | tttttttttt ttttttttga | 1380 |
| aacggagtct | tgctctgtcg | cccaggctgg | agtgcagtgg | cgcggtcttg gctcactgca | 1440 |
| agctccgtct | cccgggttca | cgccattctc | ctgcctcagc | ctcccgagca gctgggacta | 1500 |
| caggcgcccg | ccacctcgcc | cggctaatat | tttgtatttt | tagtagagac ggggtttcac | 1560 |
| tgtgttagcc | aggatggtct | cgatctcctg | accttgtgat | ccacccgcct cggcctccca | 1620 |
| aacagctggg | atttacaggc | gtgagccacc | gcgccctgcc | tagaaaagac attttaataa | 1680 |
| ccttggctgc | cgtctctggc | tatagataag | tagatctaat | actagtttgg atatctttag | 1740 |
| ggtttagaat | ctaacctcaa | gaataagaaa | tacaagtaca | aattggtgat gaagatgtat | 1800 |

| | |
|---|---:|
| tcgtattgtt tgggattggg aggctttgct tattttttaa aaactattga ggtaaagggt | 1860 |
| taagctgtaa catacttaat tgatttctta ccgttttgg ctctgttttg ctatatcccc | 1920 |
| taatttgttg gttgtgctaa tctttgtaga aagaggtctc gtatttgctg catcgtaatg | 1980 |
| acatgagtac tgctttagtt ggtttaagtt caaatgaatg aaacaactat ttttccttta | 2040 |
| gttgatttta ccctgatttc accgagtgtt tcaatgagta aatatacagc ttaaacat | 2098 |

<210> SEQ ID NO 4
<211> LENGTH: 4014
<212> TYPE: DNA
<213> ORGANISM: Homo sapiens

<400> SEQUENCE: 4

| | |
|---|---:|
| gtgcggggga agatgtagca gcttcttctc cgaaccaacc ctttgccttc ggacttctcc | 60 |
| ggggccagca gccgcccgac caggggcccg gggccacggg ctcagccgac gaccatgggc | 120 |
| tccgtgtcca accagcagtt tgcaggtggc tgcgccaagg cggcagaaga ggcgcccgag | 180 |
| gaggcgccgg aggacgcggc ccgggcggcg gacgagcctc agctgctgca cggtgcgggc | 240 |
| atctgtaagt ggttcaacgt gcgcatgggg ttcggcttcc tgtccatgac cgcccgcgcc | 300 |
| ggggtcgcgc tcgaccccc agtggatgtc tttgtgcacc agagtaagct gcacatggaa | 360 |
| gggttccgga gcttgaagga gggtgaggca gtggagttca cctttaagaa gtcagccaag | 420 |
| ggtctggaat ccatccgtgt caccggacct ggtggagtat tctgtattgg gagtgagagg | 480 |
| cggccaaaag gaaagagcat gcagaagcgc agatcaaaag gagacaggtg ctacaactgt | 540 |
| ggaggtctag atcatcatgc caaggaatgc aagctgccac cccagcccaa gaagtgccac | 600 |
| ttctgccaga gcatcagcca tatggtagcc tcatgtccgc tgaaggccca gcagggccct | 660 |
| agtgcacagg gaaagccaac ctactttcga gaggaagaag aagaaatcca cagccctacc | 720 |
| ctgctcccgg aggcacagaa ttgagccaca atgggtgggg ctattctttt tgctatcagg | 780 |
| aagttttgag gagcaggcag agtggagaaa gtgggaatag ggtgcattgg ggctagttgg | 840 |
| cactgccatg tatctcaggc ttgggttcac accatcaccc tttcttccct ctaggtgggg | 900 |
| ggaaagggtg agtcaaagga actccaacca tgctctgtcc aaatgcaagt gagggttctg | 960 |
| ggggcaacca ggaggggga atcaccctac aacctgcata ctttgagtct ccatccccag | 1020 |
| aatttccagc ttttgaaagt ggcctggata gggaagttgt tttccttta aagaaggata | 1080 |
| tataataatt cccatgccag agtgaaatga ttaagtataa gaccagattc atggagccaa | 1140 |
| gccactacat tctgtggaag gagatctctc aggagtaagc attgttttt tttcacatct | 1200 |
| tgtatcctca tacccacttt tgggatagg tgctggcagc tgtcccaagc aatgggtaat | 1260 |
| gatgatggca aaaagggtgt ttgggggaac agctgcagac ctgctgctct atgctcaccc | 1320 |
| ccgcccatt ctgggccaat gtgatttat ttatttgctc ccttggatac tgcaccttgg | 1380 |
| gtcccacttt ctccaggatg ccaactgcac tagctgtgtg cgaatgacgt atcttgtgca | 1440 |
| ttttaacttt ttttccttaa tataaatatt ctggttttgt attttgtat attttaatct | 1500 |
| aaggccctca tttcctgcac tgtgttctca ggtacatgag caatctcagg gatagccagc | 1560 |
| agcagctcca ggtctgcgca gcaggaatta ctttttgttg tttttgccac cgtggagagc | 1620 |
| aactatttgg agtgcacagc ctattgaact acctcatttt tgccaataag agctggcttt | 1680 |
| tctgccatag tgtcctcttg aaacccctc tgccttgaaa atgttttatg ggagactagg | 1740 |
| ttttaactgg gtgccccat gacttgattg ccttctactg gaagattggg aattagtcta | 1800 |
| aacaggaaat ggtggtacac agaggctagg agaggctggg cccggtgaaa aggccagaga | 1860 |

```
gcaagccaag attaggtgag ggttgtctaa tcctatggca caggacgtgc tttacatctc    1920
cagatctgtt cttcaccaga ttaggttagg cctaccatgt gccacagggt gtgtgtgtgt    1980
ttgtaaaact agagttgcta aggataagtt taaagaccaa tacccctgta cttaatcctg    2040
tgctgtcgag ggatggatat atgaagtaag gtgagatcct taacctttca aaattttcgg    2100
gttccaggga gacacacaag cgaggggtttt gtggtgcctg gagcctgtgt cctgccctgc    2160
tacagtagtg attaatagtg tcatggtagc taaaggagaa aaaggggggtt tcgtttacac    2220 gctgtgagat caccgcaaac ctaccttact gtgttgaaac gggacaaatg caatagaacg    2280
cattgggtgg tgtgtgtctg atcctgggtt cttgtctccc ctaaatgctg cccccaagt    2340 tactgtattt gtctgggctt tgtaggactt cactacgttg attgctaggt ggcctagttt    2400
gtgtaaatat aatgtattgg tctttctccg tgttctttgg gggttttgtt tacaaacttc    2460
tttttgtatt gagagaaaaa tagccaaagc atctttgaca gaaggttctg caccaggcaa    2520
aaagatctga aacattagtt tggggggccc tcttcttaaa gtgggatctt tgaaccatcc    2580
tttcttttgt attccccttc ccctattacc tattagacca gatcttctgt cctaaaaact    2640
tgtcttctac cctgccctct tttctgttca cccccaaaag aaaacttaca cacccacaca    2700
catacacatt tcatgcttgg agtgtctcca caactcttaa atgatgtatg caaaaatact    2760
gaagctagga aaaccctcca tcccttgttc ccaacctcct aagtcaagac cattaccatt    2820 tctttcttttc ttttttttttt tttttaaaaa tggagtctca ctgtgtcacc caggctggag    2880
tgcagtggca tgatcggctc actgcagcct ctgcctcttg ggttcaagtg attctcctgc    2940
ctcagcctcc tgagtagctg ggatttcagg cacccgccac actcagctaa ttttttgtatt    3000 tttagtagag acggggtttc accatgttgt ccaggctggt ctggaactcc tgacctcagg    3060
tgatctgccc accttggctt cccaaagtgc tgggattaca ggcatgagcc accatgctgg    3120
gccaaccatt tcttggtgta ttcatgccaa acacttaaga cactgctgta gcccaggcgc    3180
ggtggctcac acctgtaatc ccagcacttt ggaaggctga ggcgggcgga tcacaaggtc    3240
acgagttcaa aactatcctg gccaacacag tgaaaccccg tctctactaa aatacaaaaa    3300
aattagccgg gtgtggtggt gcatgccttt agtcctagct attcaggagg ctgaggcagg    3360
ggaatcgctt gaacccgaga ggcagaggtt gcagtgagct gagatcgcac cactgcactc    3420
cagcctggtt acagagcaag actctgtctc aaacaaaaca aaacaaaaca aaacacact    3480 actgtattttt ggatggatca aacctcctta atttttaattt ctaatcctaa agtaaagaga    3540
tgcaattggg ggccttccat gtagaaagtg gggtcaggag gccaagaaag ggaatatgaa    3600
tgtatatcca agtcactcag gaactttttat gcaggtgcta gaaactttat gtcaaagtgg    3660
ccacaagatt gtttaatagg agacgaacga atgtaactcc atgtttactg ctaaaaacca    3720
aagctttgtg taaaatcttg aatttatggg gcgggagggt aggaaagcct gtacctgtct    3780 gttttttttcc tgatccttttt ccctcattcc tgaactgcag gagactgagc cccttttgggc    3840 tttggtgacc ccatcactgg ggtgtgttta tttgatggtt gattttgctg tactgggtac    3900
ttcctttccc attttctaat catttttttaa cacaagctga ctcttccctt cccttctcct    3960
ttccctggga aaatacaatg aataaataaa gacttattgg tacgcaaact gtca          4014
```

<210> SEQ ID NO 5
<211> LENGTH: 2377
<212> TYPE: DNA
<213> ORGANISM: Homo sapiens

<400> SEQUENCE: 5

```
accccccgagc tgtgctgctc gcggccgcca ccgccgggcc ccggccgtcc ctggctcccc    60
tcctgcctcg agaagggcag ggcttctcag aggcttggcg ggaaaaagaa cggagggagg   120
gatcgcgctg agtataaaag ccggttttcg gggctttatc taactcgctg tagtaattcc   180
agcgagaggc agagggagcg agcgggcggc cggctagggt ggaagagccg ggcgagcaga   240
gctgcgctgc gggcgtcctg ggaagggaga tccggagcga ataggggggct tcgcctctgg   300
cccagccctc ccgctgatcc cccagccagc ggtccgcaac ccttgccgca tccacgaaac   360
tttgcccata gcagcgggcg ggcactttgc actggaactt acaacacccg agcaaggacg   420
cgactctccc gacgcgggga ggctattctg cccatttggg gacacttccc cgccgctgcc   480
aggacccgct tctctgaaag gctctccttg cagctgctta gacgctggat tttttttcggg   540
tagtggaaaa ccagcagcct cccgcgacga tgcccctcaa cgttagcttc accaacagga   600
actatgacct cgactacgac tcggtgcagc cgtatttcta ctgcgacgag gaggagaact   660
tctaccagca gcagcagcag agcgagctgc agccccggc gccagcgag atatctgga    720
agaaattcga gctgctgccc accccgcccc tgtcccctag ccgccgctcc gggctctgct   780
cgccctccta cgttgcggtc acaccttct cccttcgggg agacaacgac ggcggtggcg   840
ggagcttctc cacggccgac cagctggaga tggtgaccga gctgctggga ggagacatgg   900
tgaaccagag tttcatctgc gacccggacg acgagacctt catcaaaaac atcatcatcc   960
aggactgtat gtggagcggc ttctcggccg ccgccaagct cgtctcagag aagctggcct  1020
cctaccaggc tgcgcgcaaa gacagcgca gcccgaaccc cgccgcggc cacagcgtct  1080
gctccacctc cagcttgtac ctgcaggatc tgagcgccgc cgcctcagag tgcatcgacc  1140
cctcggtggt cttcccctac cctctcaacg acagcagctc gccaagtcc tgcgcctcgc  1200
aagactccag cgccttctct ccgtcctcgg attctctgct ctcctcgacg gagtcctccc  1260
cgcagggcag ccccgagccc ctggtgctcc atgaggagac accgccacc accagcagcg  1320
actctgagga ggaacaagaa gatgaggaag aaatcgatgt tgtttctgtg gaaagaggc   1380
aggctcctgg caaaggtca gagtctggat caccttctgc tggaggccac agcaaacctc  1440
ctcacagccc actggtcctc aagaggtgcc acgtctccac acatcagcac aactacgcag  1500
cgcctccctc cactcggaag gactatcctg ctgccaagag ggtcaagttg gacagtgtca  1560
gagtcctgag acagatcagc aacaaccgaa aatgcaccag ccccaggtcc tcggacaccg  1620
aggagaatgt caagaggcga acacacaacg tcttggagcg ccagaggagg aacgagctaa  1680
aacggagctt ttttgccctg cgtgaccaga tcccggagtt ggaaaacaat gaaaaggccc  1740
ccaaggtagt tatccttaaa aaagccacag catacatcct gtccgtccaa gcagaggagc  1800
aaaagctcat ttctgaagag gacttgttgc ggaaacgacg agaacagttg aaacacaaac  1860
ttgaacagct acggaactct tgtgcgtaag gaaagtaag gaaaacgatt ccttctaaca   1920
gaaatgtcct gagcaatcac ctatgaactt gtttcaaatg catgatcaaa tgcaacctca  1980
caaccttggc tgagtcttga gactgaaaga tttagccata atgtaaactg cctcaaattg  2040
gactttgggc ataaaagaac tttttatgc ttaccatctt tttttttct ttaacagatt   2100
tgtatttaag aattgttttt aaaaaatttt aagatttaca caatgtttct ctgtaaatat  2160
tgccattaaa tgtaaataac tttaataaaa cgtttatagc agttacacag aatttcaatc  2220
ctagtatata gtacctagta ttataggtac tataaaccct aatttttttt atttaagtac  2280
attttgcttt ttaaagttga ttttttttcta ttgtttttag aaaaaataaa ataactggca  2340
aatatatcat tgagccaaaa aaaaaaaaaa aaaaaaa                            2377
```

<210> SEQ ID NO 6
<211> LENGTH: 2949
<212> TYPE: DNA
<213> ORGANISM: Homo sapiens

<400> SEQUENCE: 6

| | | | | | |
|---|---|---|---|---|---|
| agtttcccga | ccagagagaa | cgaacgtgtc | tgcgggcgcg | cggggagcag | aggcggtggc | 60 |
| gggcggcggc | ggcaccggga | gccgccgagt | gaccctcccc | cgcccctctg | gccccccacc | 120 |
| ctcccacccg | cccgtggccc | gcgcccatgg | ccgcgcgcgc | tccacacaac | tcaccggagt | 180 |
| ccgcgccttg | cgccgccgac | cagttcgcag | ctccgcgcca | cggcagccag | tctcacctgg | 240 |
| cggcaccgcc | cgcccaccgc | cccggccaca | gccctgcgc | ccacggcagc | actcgaggcg | 300 |
| accgcgacag | tggtggggga | cgctgctgag | tggaagagag | cgcagcccgg | ccaccggacc | 360 |
| tacttactcg | ccttgctgat | tgtctatttt | tgcgtttaca | acttttctaa | gaacttttgt | 420 |
| atacaaagga | acttttttaaa | aaagacgctt | ccaagttata | tttaatccaa | agaagaagga | 480 |
| tctcggccaa | tttggggttt | tgggttttgg | cttcgtttct | tctcttcgtt | gactttgggg | 540 |
| ttcaggtgcc | ccagctgctt | cgggctgccg | aggaccttct | gggcccccac | attaatgagg | 600 |
| cagccacctg | gcgagtctga | catggctgtc | agcgacgcgc | tgctcccatc | tttctccacg | 660 |
| ttcgcgtctg | gccggcggg | aagggagaag | acactgcgtc | aagcaggtgc | ccgaataac | 720 |
| cgctggcggg | aggagctctc | ccacatgaag | cgacttcccc | cagtgcttcc | cggccgcccc | 780 |
| tatgaccggg | cggcggcgac | cgtggccaca | gacctggaga | gcggcggagc | cggtgcggct | 840 |
| tgcggcggta | gcaacctggc | gccctacct | cggagagaga | ccgaggagtt | caacgatctc | 900 |
| ctggacctgg | actttattct | ctccaattcg | ctgacccatc | ctccggagtc | agtggccgcc | 960 |
| accgtgtcct | cgtcagcgtc | agcctcctct | tcgtcgtcgc | cgtcgagcag | cggccctgcc | 1020 |
| agcgcgccct | ccacctgcag | cttcacctat | ccgatccggg | ccgggaacga | cccgggcgtg | 1080 |
| gcgccgggcg | gcacgggcgg | aggcctcctc | tatggcaggg | agtccgctcc | ccctccgacg | 1140 |
| gctcccttca | acctggcgga | catcaacgac | gtgagcccct | cgggcggctt | cgtggccgag | 1200 |
| ctcctgcggc | cagaattgga | cccggtgtac | attccgccgc | agcagccgca | gccgccaggt | 1260 |
| ggcgggctga | tggcaagtt | cgtgctgaag | gcgtcgctga | gcgcccctgg | cagcgagtac | 1320 |
| ggcagcccgt | cggtcatcag | cgtcagcaaa | ggcagccctg | acggcagcca | cccggtggtg | 1380 |
| gtggcgccct | acaacggcgg | gccgccgcgc | acgtgcccca | agatcaagca | ggaggcggtc | 1440 |
| tcttcgtgca | cccacttggg | cgctggaccc | cctctcagca | atggccaccg | gccggctgca | 1500 |
| cacgacttcc | ccctggggcg | gcagctcccc | agcaggacta | ccccgaccct | gggtcttgag | 1560 |
| gaagtgctga | gcagcaggga | ctgtcaccct | gccctgccgc | ttcctcccgg | cttccatccc | 1620 |
| cacccggggc | caattaccc | atccttcctg | cccgatcaga | tgcagccgca | agtcccgccg | 1680 |
| ctccattacc | aagagctcat | gccacccggt | tcctgcatgc | cagaggagcc | caagccaaag | 1740 |
| aggggaagac | gatcgtggcc | ccggaaaagg | accgccaccc | acacttgtga | ttacgcgggc | 1800 |
| tgcggcaaaa | cctacacaaa | gagttcccat | ctcaaggcac | acctgcgaac | ccacacaggt | 1860 |
| gagaaaccct | ccactgtga | ctgggacggc | tgtggatgga | aattcgcccg | ctcagatgaa | 1920 |
| ctgaccaggc | actaccgtaa | acacacgggg | caccgcccgt | tccagtgcca | aaaatgcgac | 1980 |
| cgagcatttt | ccaggtcgga | ccacctcgcc | ttacacatga | agaggcattt | ttaaatccca | 2040 |
| gacagtggat | atgaccccaca | ctgccagaag | agaattcagt | atttttact | tttcacactg | 2100 |
| tcttcccgat | gagggaagga | gcccagccag | aaagcactac | aatcatggtc | aagttcccaa | 2160 |

| | |
|---|---|
| ctgagtcatc ttgtgagtgg ataatcagga aaaatgagga atccaaaaga caaaaatcaa | 2220 |
| agaacagatg gggtctgtga ctggatcttc tatcattcca attctaaatc cgacttgaat | 2280 |
| attcctggac ttacaaaatg ccaaggggt gactggaagt tgtggatatc agggtataaa | 2340 |
| ttatatccgt gagttggggg agggaagacc agaattccct tgaattgtgt attgatgcaa | 2400 |
| tataagcata aaagatcacc ttgtattctc tttaccttct aaaagccatt attatgatgt | 2460 |
| tagaagaaga ggaagaaatt caggtacaga aaacatgttt aaatagccta aatgatggtg | 2520 |
| cttggtgagt cttggttcta aaggtaccaa acaaggaagc caagttttc aaactgctgc | 2580 |
| atactttgac aaggaaaatc tatatttgtc ttccgatcaa catttatgac ctaagtcagg | 2640 |
| taatataccct ggtttacttc tttagcattt ttatgcagac agtctgttat gcactgtggt | 2700 |
| ttcagatgtg caataatttg tacaatggtt tattcccaag tatgccttaa gcagaacaaa | 2760 |
| tgtgttttc tatatagttc cttgccttaa taaatatgta atataaattt aagcaaacgt | 2820 |
| ctatttgta tatttgtaaa ctacaaagta aaatgaacat tttgtggagt ttgtattttg | 2880 |
| catactcaag gtgagaatta agttttaaat aaacctataa tattttatct gaaaaaaaaa | 2940 |
| aaaaaaaaa | 2949 |

<210> SEQ ID NO 7
<211> LENGTH: 2949
<212> TYPE: DNA
<213> ORGANISM: Simian virus 40

<400> SEQUENCE: 7

| | |
|---|---|
| agtttcccga ccagagagaa cgaacgtgtc tgcgggcgcg cggggagcag aggcggtggc | 60 |
| gggcggcggc ggcaccggga gccgccgagt gaccctcccc cgcccctctg gcccccacc | 120 |
| ctcccacccg cccgtggccc gcgcccatgg ccgcgcgcgc tccacacaac tcaccggagt | 180 |
| ccgcgccttg cgccgccgac cagttcgcag ctccgcgcca cggcagccag tctcacctgg | 240 |
| cggcaccgcc cgcccaccgc cccggccaca gcccctgcgc ccacggcagc actcgaggcg | 300 |
| accgcgacag tggtgggga cgctgctgag tggaagagag cgcagcccgg ccaccggacc | 360 |
| tacttactcg ccttgctgat tgtctatttt tgcgtttaca acttttctaa gaacttttgt | 420 |
| atacaaagga acttttaaa aaagacgctt ccaagttata tttaatccaa agaagaagga | 480 |
| tctcggccaa tttgggtttt tgggttttgg cttcgttct tctcttcgtt gactttgggg | 540 |
| ttcaggtgcc ccagctgctt cgggctgccg aggaccttct gggccccac attaatgagg | 600 |
| cagccacctg gcgagtctga catggctgtc agcgacgcgc tgctcccatc tttctccacg | 660 |
| ttcgcgtctg gcccggcggg aagggagaag acactgcgtc aagcaggtgc cccgaataac | 720 |
| cgctggcggg aggagctctc ccacatgaag cgacttcccc cagtgcttcc cggccgcccc | 780 |
| tatgaccctgg cggcggcgac cgtggccaca gacctggaga gcggcggagc cggtgcggct | 840 |
| tgcggcggta gcaacctggc gcccctacct cggagagaga ccgaggagtt caacgatctc | 900 |
| ctggacctgg actttattct ctccaattcg ctgacccatc ctccggagtc agtggccgcc | 960 |
| accgtgtcct cgtcagcgtc agcctcctct tcgtcgtcgc cgtcgagcag cggccctgcc | 1020 |
| agcgcgccct ccacctgcag cttcacctat ccgatccggg ccgggaacga ccccgggcgtg | 1080 |
| gcgcggggcg gcacgggcgg aggcctcctc tatgcaggg agtccgctcc ccctccgacg | 1140 |
| gctcccttca acctggcgga catcaacgac gtgagcccct cgggcggctt cgtggccgag | 1200 |
| ctcctgcggg cagaattgga cccggtgtac attccgccgc agcagccgca gccgccaggt | 1260 |
| ggcgggctga tgggcaagtt cgtgctgaag gcgtcgctga cgcgccctgg cagcgagtac | 1320 |

```
ggcagcccgt cggtcatcag cgtcagcaaa ggcagccctg acggcagcca cccggtggtg    1380
gtggcgccct acaacggcgg gccgccgcgc acgtgcccca agatcaagca ggaggcggtc    1440
tcttcgtgca cccacttggg cgctggaccc cctctcagca atggccaccg gccggctgca    1500
cacgacttcc ccctggggcg gcagctcccc agcaggacta ccccgaccct gggtcttgag    1560
gaagtgctga gcagcaggga ctgtcaccct gccctgccgc ttcctcccgg cttccatccc    1620
caccccgggc ccaattaccc atccttcctg cccgatcaga tgcagccgca agtcccgccg    1680
ctccattacc aagagctcat gccacccggt tcctgcatgc cagaggagcc caagccaaag    1740
aggggaagac gatcgtggcc ccggaaaagg accgccaccc acacttgtga ttacgcgggc    1800
tgcggcaaaa cctacacaaa gagttcccat ctcaaggcac acctgcgaac ccacacaggt    1860
gagaaacctt accactgtga ctgggacggc tgtggatgga aattcgcccg ctcagatgaa    1920
ctgaccaggc actaccgtaa acacacgggg caccgcccgt tccagtgcca aaaatgcgac    1980
cgagcatttt ccaggtcgga ccacctcgcc ttacacatga agaggcattt ttaaatccca    2040
gacagtggat atgacccaca ctgccagaag agaattcagt atttttttact tttcacactg    2100 tcttcccgat gagggaagga gcccagccag aaagcactac aatcatggtc aagttcccaa    2160
ctgagtcatc ttgtgagtgg ataatcagga aaatgagga atccaaaaga caaaaatcaa    2220
agaacagatg gggtctgtga ctggatcttc tatcattcca attctaaatc cgacttgaat    2280
attcctggac ttacaaaatg ccaagggggt gactggaagt tgtggatatc agggtataaa    2340
ttatatccgt gagttggggg agggaagacc agaattccct tgaattgtgt attgatgcaa    2400
tataagcata aagatcacc ttgtattctc tttaccttct aaaagccatt attatgatgt    2460
tagaagaaga ggaagaaatt caggtacaga aaacatgttt aaatagccta atgatggtg    2520 cttggtgagt cttggttcta aaggtaccaa acaaggaagc caagttttc aaactgctgc    2580 atactttgac aaggaaaatc tatatttgtc ttccgatcaa catttatgac ctaagtcagg    2640
taatatacct ggtttacttc tttagcattt ttatgcagac agtctgttat gcactgtggt    2700
ttcagatgtg caataatttg tacaatggtt tattcccaag tatgccttaa gcagaacaaa    2760 tgtgttttc tatatagttc cttgccttaa taaatatgta atataaattt aagcaaacgt    2820
ctattttgta tatttgtaaa ctacaaagta aaatgaacat tttgtggagt ttgtattttg    2880
catactcaag gtgagaatta agttttaaat aaacctataa tattttatct gaaaaaaaaa    2940
aaaaaaaaa                                                           2949

<210> SEQ ID NO 8
<211> LENGTH: 4018
<212> TYPE: DNA
<213> ORGANISM: Homo sapiens

<400> SEQUENCE: 8
caggcagcgc tgcgtcctgc tgcgcacgtg ggaagccctg gccccggcca ccccgcgat     60 gccgcgcgct ccccgctgcc gagccgtgcg ctccctgctg cgcagccact accgcgaggt    120
gctgccgctg ccacgttcg tgcggcgcct ggggccccag ggctggcggc tggtgcagcg    180
cggggacccg gcggctttcc gcgcgctggt ggcccagtgc ctggtgtgcg tgccctggga    240
cgcacggccc ccccgccg ccccctcctt cgccaggtc tcctgcctga aggagctggt    300
ggcccgagtg ctgcagaggc tgtgcgagcg cggcgcgaag aacgtgctgg ccttcggctt    360
cgcgctgctg gacggggccc gcggggccc cccgaggcc ttcaccacca gcgtgcgcag    420
ctacctgccc aacacggtga ccgacgcact gcgggggagc ggggcgtggg ggctgctgct    480
```

```
gcgccgcgtg ggcgacgacg tgctggttca cctgctggca cgctgcgcgc tctttgtgct    540
ggtggctccc agctgcgcct accaggtgtg cgggccgccg ctgtaccagc tcggcgctgc    600
cactcaggcc cggcccccgc cacacgctag tggaccccga aggcgtctgg gatgcgaacg    660
ggcctggaac catagcgtca gggaggccgg ggtccccctg ggcctgccag ccccgggtgc    720
gaggaggcgc ggggggcagtg ccagccgaag tctgccgttg cccaagaggc caggcgtgg    780 cgctgcccct gagccggagc ggacgcccgt tgggcagggg tcctgggccc acccgggcag    840
gacgcgtgga ccgagtgacc gtggtttctg tgtggtgtca cctgccagac ccgccgaaga    900
agccacctct ttggagggtg cgctctctgg cacgcgccac tcccacccat ccgtgggccg    960
ccagcaccac gcgggcccc catccacatc gcggccacca cgtccctggg acacgccttg   1020
tcccccggtg tacgccgaga ccaagcactt cctctactcc tcaggcgaca aggagcagct   1080
gcggccctcc ttcctactca gctctctgag gcccagcctg actggcgctc ggaggctcgt   1140
ggagaccatc tttctgggtt ccaggccctg gatgccaggg actccccgca ggttgccccg   1200
cctgccccag cgctactggc aaatgcggcc cctgtttctg gagctgcttg gaaccacgc    1260 gcagtgccc tacggggtgc tcctcaagac gcactgccg ctgcgagctg cggtcacccc    1320
agcagccggt gtctgtgccc gggagaagcc cagggctct gtggcggccc ccgaggagga   1380
ggacacagac ccccgtcgcc tggtgcagct gctccgccag cacagcagcc cctggcaggt   1440
gtacggcttc gtgcgggcct gctgcgccg gctggtgccc ccaggcctct ggggctccag   1500
gcacaacgaa cgccgcttcc tcaggaacac caagaagttc atctccctgg ggaagcatgc   1560
caagctctcg ctgcaggagc tgacgtggaa gatgagcgtg cgggactgcg cttggctgcg   1620
caggagccca ggggttggct gtgttccggc cgcagagcac cgtctgcgtg aggagatcct   1680
ggccaagttc ctgcactggc tgatgagtgt gtacgtcgtc gagctgctca ggtctttctt   1740
ttatgtcacg gagaccacgt ttcaaaagaa caggctcttt ttctaccgga agagtgtctg   1800
gagcaagttg caaagcattg gaatcagaca gcacttgaag agggtgcagc tgcgggagct   1860
gtcggaagca gaggtcaggc agcatcggga agccaggccc gccctgctga cgtccagact   1920
ccgcttcatc cccaagcctg acgggctgcg gccgattgtg aacatggact acgtcgtggg   1980
agccagaacg ttccgcagag aaaagagggc cgagcgtctc acctcgaggg tgaaggcact   2040
gttcagcgtg ctcaactacg agcgggcgcg gcgccccggc ctcctgggcg cctctgtgct   2100
gggcctggac gatatccaca gggcctggcg caccttcgtg ctgcgtgtgc gggcccagga   2160
cccgccgcct gagctgtact tgtcaaggt ggatgtgacg ggcgcgtacg acaccatccc    2220
ccaggacagg ctcacggagg tcatcgccag catcatcaaa ccccagaaca cgtactgcgt   2280
gcgtcggtat gccgtggtcc agaaggccgc ccatgggcac gtccgcaagg ccttcaagag   2340
ccacgtctct accttgacag acctccagcc gtacatgcga cagttcgtgg ctcacctgca   2400
ggagaccagc ccgctgaggg atgccgtcgt catcgagcag agctcctccc tgaatgaggc   2460
cagcagtggc ctcttcgacg tcttcctacg cttcatgtgc caccacgccg tgcgcatcag   2520
gggcaagtcc tacgtccagt gccaggggat cccgcagggc tccatcctct ccacgctgct   2580
ctgcagcctg tgctacggcg acatggagaa caagctgttt gcggggattc ggcgggacgg   2640
gctgctcctg cgtttggtgg atgatttctt gttggtgaca cctcacctca cccacgcgaa   2700
aaccttcctc aggaccctgg tccgaggtgt ccctgagtat ggctgcgtgg tgaacttgcg   2760
gaagacagtg gtgaacttcc ctgtagaaga cgaggccctg ggtggcacgg cttttgttca   2820
gatgccggcc cacggcctat tcccctggtg cggcctgctg ctggataccc ggaccctgga   2880
```

-continued

```
ggtgcagagc gactactcca gctatgcccg gacctccatc agagccagtc tcaccttcaa    2940
ccgcggcttc aaggctggga ggaacatgcg tcgcaaactc tttggggtct tgcggctgaa    3000
gtgtcacagc ctgttcctgg atttgcaggt gaacagcctc cagacggtgt gcaccaacat    3060
ctacaagatc ctcctgctgc aggcgtacag gtttcacgca tgtgtgctgc agctcccatt    3120
tcatcagcaa gtttggaaga accccacatt tttcctgcgc gtcatctctg acacggcctc    3180
cctctgctac tccatcctga agccaagaa cgcagggatg tcgctggggg ccaagggcgc    3240
cgccggccct ctgccctccg aggccgtgca gtggctgtgc caccaagcat tcctgctcaa    3300
gctgactcga caccgtgtca cctacgtgcc actcctgggg tcactcagga cagcccagac    3360
gcagctgagt cggaagctcc cggggacgac gctgactgcc ctggaggccg cagccaaccc    3420
ggcactgccc tcagacttca agaccatcct ggactgatgg ccacccgccc acagccaggc    3480
cgagagcaga caccagcagc cctgtcacgc cgggctctac gtcccaggga gggaggggcg    3540
gcccacaccc aggcccgcac cgctgggagt ctgaggcctg agtgagtgtt tggccgaggc    3600
ctgcatgtcc ggctgaaggc tgagtgtccg gctgaggcct gagcgagtgt ccagccaagg    3660
gctgagtgtc cagcacacct gccgtcttca cttccccaca ggctggcgct cggctccacc    3720
ccagggccag cttttcctca ccaggagccc ggcttccact ccccacatag gaatagtcca    3780
tccccagatt cgccattgtt cacccctcgc cctgccctcc tttgcttcc accccacca    3840 tccaggtgga gaccctgaga aggaccctgg gagctctggg aatttggagt gaccaaggt    3900 gtgccctgta cacaggcgag gaccctgcac ctggatgggg gtccctgtgg gtcaaattgg    3960
ggggaggtgc tgtgggagta aaatactgaa tatatgagtt tttcagtttt gaaaaaaa    4018

<210> SEQ ID NO 9
<211> LENGTH: 90
<212> TYPE: DNA
<213> ORGANISM: Foot-and-mouth disease virus

<400> SEQUENCE: 9
ggttccggaa aaattgtcgc tcctgtcaaa caaactctta actttgattt actcaaactg    60
gctggggatg tagaaagcaa tccaggtcca                                     90

<210> SEQ ID NO 10
<211> LENGTH: 589
<212> TYPE: DNA
<213> ORGANISM: Cytomegalovirus

<400> SEQUENCE: 10
tagttattaa tagtaatcaa ttacggggtc attagttcat agcccatata tggagttccg    60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatc                589
```

<210> SEQ ID NO 11
<211> LENGTH: 1192
<212> TYPE: DNA
<213> ORGANISM: Homo sapiens

<400> SEQUENCE: 11

```
ctagcttcgt gaggctccgg tgcccgtcag tgggcagagc gcacatcgcc cacagtcccc      60
gagaagttgg ggggaggggt cggcaattga accggtgcct agagaaggtg gcgcggggta     120
aactgggaaa gtgatgtcgt gtactggctc cgccttttc ccgagggtgg gggagaaccg     180
tatataagtg cagtagtcgc cgtgaacgtt cttttcgca acgggtttgc cgccagaaca     240
caggtaagtg ccgtgtgtgg ttcccgcggg cctggcctct ttacgggtta tggcccttgc     300
gtgccttgaa ttacttccac ctggctccag tacgtgattc ttgatcccga gctggagcca     360
ggggcgggcc ttgcgcttta ggagccccctt cgcctcgtgc ttgagttgag gcctggcctg     420
gcgctgggg ccgccgcgtg cgaatctggt ggccttcg cgcctgtctc gctgctttcg     480
ataagtctct agccatttaa aattttgat gacctgctgc gacgcttttt ttctggcaag     540
atagtcttgt aaatgcgggc caggatctgc acactggtat ttcggttttt gggcccgcgg     600
ccggcgacgg ggcccgtgcg tcccagcgca catgttcggc gaggcgggc ctgcgagcgc     660
ggccaccgag aatcggacgg gggtagtctc aagctggccg gcctgctctg gtgcctggcc     720
tcgcgccgcc gtgtatcgcc ccgccctggg cggcaaggct ggcccggtcg gcaccagttg     780
cgtgagcgga aagatggccg cttcccggcc ctgctccagg gggctcaaaa tggaggacgc     840
ggcgctcggg agagcgggcg ggtgagtcac ccacacaaag gaaagggcc tttccgtcct     900
cagccgtcgc ttcatgtgac tccacggagt accgggcgcc gtccaggcac ctcgattagt     960
tctggagctt ttggagtacg tcgtctttag gttggggga ggggttttat gcgatggagt    1020
ttccccacac tgagtgggtg gagactgaag ttaggccagc ttggcacttg atgtaattct    1080
cgttggaatt tgcccctttt gagtttggat cttggttcat tctcaagcct cagacagtgg    1140
ttcaaagttt ttttcttcca tttcaggtgt cgtgaacacg tggtcgcggc ca           1192
```

<210> SEQ ID NO 12
<211> LENGTH: 1192
<212> TYPE: DNA
<213> ORGANISM: Homo sapiens

<400> SEQUENCE: 12

```
ctagcttcgt gaggctccgg tgcccgtcag tgggcagagc gcacatcgcc cacagtcccc      60
gagaagttgg ggggaggggt cggcaattga accggtgcct agagaaggtg gcgcggggta     120
aactgggaaa gtgatgtcgt gtactggctc cgccttttc ccgagggtgg gggagaaccg     180
tatataagtg cagtagtcgc cgtgaacgtt cttttcgca acgggtttgc cgccagaaca     240
caggtaagtg ccgtgtgtgg ttcccgcggg cctggcctct ttacgggtta tggcccttgc     300
gtgccttgaa ttacttccac ctggctccag tacgtgattc ttgatcccga gctggagcca     360
ggggcgggcc ttgcgcttta ggagccccctt cgcctcgtgc ttgagttgag gcctggcctg     420
ggcgctgggg ccgccgcgtg cgaatctggt ggccttcg cgcctgtctc gctgctttcg     480
ataagtctct agccatttaa aattttgat gacctgctgc gacgcttttt ttctggcaag     540
atagtcttgt aaatgcgggc caggatctgc acactggtat ttcggttttt gggcccgcgg     600
ccggcgacgg ggcccgtgcg tcccagcgca catgttcggc gaggcgggc ctgcgagcgc     660
ggccaccgag aatcggacgg gggtagtctc aagctggccg gcctgctctg gtgcctggcc     720
tcgcgccgcc gtgtatcgcc ccgccctggg cggcaaggct ggcccggtcg gcaccagttg     780
```

```
                                            -continued
cgtgagcgga aagatggccg cttcccggcc ctgctccagg gggctcaaaa tggaggacgc      840
ggcgctcggg agagcgggcg ggtgagtcac ccacacaaag gaaaagggcc tttccgtcct      900
cagccgtcgc ttcatgtgac tccacggagt accgggcgcc gtccaggcac ctcgattagt      960
tctggagctt ttggagtacg tcgtctttag gttgggggga ggggtttttat gcgatggagt     1020 ttccccacac tgagtgggtg gagactgaag ttaggccagc ttggcacttg atgtaattct      1080
cgttggaatt tgcccttttt gagtttggat cttggttcat tctcaagcct cagacagtgg     1140
ttcaaagttt ttttcttcca tttcaggtgt cgtgaacacg tggtcgcggc ca             1192
```

OCT4 AND SOX2 WITH SV40 T ANTIGEN PRODUCE PLURIPOTENT STEM CELLS FROM PRIMATE SOMATIC CELLS

CROSS-REFERENCE TO RELATED APPLICATION

This application claims the benefit of U.S. Provisional Patent Application No. 61/108,362, filed Oct. 24, 2008, incorporated herein by reference as if set forth in its entirety.

STATEMENT REGARDING FEDERALLY SPONSORED RESEARCH OR DEVELOPMENT

This invention was made with United States government support awarded by the following agencies: NIH GM081629, RR000167. The United States government has certain rights in this invention.

BACKGROUND

Embryonic stem (ES) cells hold great promise in science and medicine due to their pluripotent nature, i.e. the ability to replicate indefinitely and differentiate into cells of all three germ layers (Thomson et al., Science 282:1145-1147 (1998), incorporated by reference herein as if set forth in its entirety). The application of human ES cells in therapy and regenerative medicine is complicated by the possibility of rejection by the recipient's immune system. Human pluripotent cells that are substantially genetically identical to a particular recipient are, thus, highly desirable. Also, genetic identity may be important for the use of ES cells in designing patient-specific treatment strategies.

First attempts to generate pluripotent cells from a post-natal primate individual employed somatic nuclear transfer (see, e.g., Byrne, JA et al., Nature 450:497-502 (2007)) and cell fusion (see, e.g., Yu, J et al., Stem Cells 24:168-176 (2006)). However, clinical use of somatic nuclear transfer is impractical due to its low efficiency, while cell fusion results in near tetraploid cells. In 2007, two groups of scientists reprogrammed somatic cells from a post-natal primate individual into pluripotent stem cells (Yu et al. Science 318:1917-1920 (2007) and Takahashi et al., Cell 131:861-872 (2007)), each incorporated by reference herein as if set forth in its entirety. Both groups delivered into, and expressed in, human somatic cells cDNA of four transcription factors using a viral vector system for expressing potency-determining transgenes. The transcription factors of Takahashi et al. were OCT4, SOX2, c-Myc, and KLF4, while Yu et al. employed OCT4, SOX2, NANOG, and LIN28. The expression of these sets of transcription factors induced human somatic cells to acquire ES cell-specific characteristics, including morphology, proliferation, and gene- and surface marker expression. Somatic cells reprogrammed in this manner are referred to as induced pluripotent (iPS) cells. The existence of iPS cells circumvents the need for blastocysts and reduces concerns associated with immune rejection.

Shortly thereafter, Lowry et al. generated patient-specific iPS cell lines through ectopic expression of OCT4, SOX2, c-Myc, and KLF4 (Lowry et al., PNAS105:2883-2888 (2008)) transgenes. More recently, iPS cells have been generated from a number of different human and murine somatic cell types, such as epithelial, fibroblast, liver, stomach, neural, and pancreatic cells. Further, iPS cells have been successfully differentiated into cells of various lineages (e.g., Dimos et al. Science 321:1218-1221 (2008)).

Current methods for generating iPS cells employ retroviral vectors such as those derived from lentivirus. These vectors stably integrate into, and permanently change, a target cell's DNA at virtually any chromosomal locus. This untargeted interaction between reprogramming vector and genome is associated with a risk of aberrant cellular gene expression as well as neoplastic growth caused by viral gene reactivation (Okita et al. Nature 448:313-317 (2007)).

Moreover, continued presence and expression of the transgenes can interfere with the recipient cell's physiology. Further, ectopic expression of transcription factors used to reprogram somatic cells, such as c-Myc, can induce programmed cell death (apoptosis) (Askew et al., Oncogene 6:1915-1922 (1991), Evan et al., Cell 69:119-128 (1992)). Furthermore, continued expression of factors such as OCT4 can interfere with subsequent differentiation of iPS cells.

It is desirable to reprogram somatic cells to a state of higher potency without altering the cells' genetic makeup beyond the reprogramming-associated alterations. Recently, Stadtfeld et al. generated murine iPS cells using a nonintegrating adenovirus that transiently expressed OCT4, SOX2, KLF4, and c-Myc (Stadtfeld et al., Sciencexpress, Sep. 25, 2008). To date, primate iPS cells generated without using retroviral vectors have not been reported.

BRIEF SUMMARY

The present invention is broadly summarized as relating to reprogramming of differentiated primate somatic cells to produce primate pluripotent cells.

In a first aspect, the invention is summarized in that a method for producing a primate pluripotent cell includes the step of delivering into a primate somatic cell a set of transgenes sufficient to reprogram the somatic cell to a pluripotent state, the transgenes being carried on at least one episomal vector that does not encode an infectious virus, and recovering pluripotent cells. References herein to a "non-viral" vector or construct indicate that the vector or construct cannot encode an infectious virus.

In a second aspect, the invention relates to an enriched population of replenishable reprogrammed pluripotent cells of a primate, including a human primate, wherein, in contrast to existing iPS cells, the at least one vector, including any element thereof having a viral source or derivation is substantially absent from the pluripotent cells. As used herein, this means that the reprogrammed cells contain fewer than one copy of the episomal vector per cell, and preferably no residual episomal vector in the cells. Because asymmetric partitioning during cell division dilutes the vector, one can readily obtain reprogrammed cells from which the vector has been lost. As noted elsewhere herein, on very rare occasions a reprogramming vector can integrate into the genome of the cell, but cells having an integrated vector can be avoided by screening for absence of the vector. Further, in contrast to existing ES cells, the primate pluripotent cells of the invention are substantially genetically identical to somatic cells from a fetal or post-natal individual. Fetal cells can be obtained from, e.g., amniotic fluid. The cells of the enriched population are not readily distinguished from existing primate ES and iPS cells morphologically (i.e., round shape, large nucleoli and scant cytoplasm) or by growth properties (i.e., doubling time; ES cells have a doubling time of about seventeen to eighteen hours). Like iPS cells and ES cells, the reprogrammed cells also express pluripotent cell-specific markers (e.g., OCT-4, SSEA-3, SSEA-4, TRA-1-60, TRA-1-81, but not SSEA-1). Unlike ES cells, the reprogrammed cells are not immediately derived from embryos. As used herein, "not immediately derived from embryos" means that the starting cell type for producing the pluripotent cells is a non-pluripotent cell, such as a multipotent cell or terminally differentiated cell, such as somatic cells obtained from a fetal or post-natal individual. Like iPS cells, the pluripotent cells produced in the method can transiently express one or more copies of selected potency-determining factors during their derivation.

Unless otherwise defined, all technical and scientific terms used herein have the same meaning as commonly understood by one of ordinary skill in the art to which this invention belongs. Although suitable materials and methods for the practice or testing of the present invention are described below, other materials and methods similar or equivalent to those described herein, which are well known in the art, can be used.

Other objectives, advantages and features of the present invention will become apparent from the following specification taken in conjunction with the accompanying drawings.

BRIEF DESCRIPTION OF THE SEVERAL VIEWS OF THE DRAWINGS

FIG. 1A-B illustrate the effect on reprogramming efficiency of different nucleotide sequences that link transgenes on the vector(s) delivered during the reprogramming methods.

FIG. 2A-C illustrate the effect on reprogramming efficiency of c-Myc, KLF-4, and SV40 large T antigen gene expression in human newborn foreskin fibroblasts.

FIG. 3A-C illustrate a suitable construct for carrying transgenes into somatic cells in accord with the method, temporal expression of an episomal vector-mediated transgene, and the effect of vector quantity on cell survival after nucleofection.

FIG. 4A-D illustrate reprogramming of human newborn foreskin fibroblasts with episomal vector-mediated transgene expression.

FIG. 5A-B illustrate related constructs harboring an expression cassette useful in the reprogramming methods of the invention.

DETAILED DESCRIPTION OF PREFERRED EMBODIMENTS

Figure 3C:
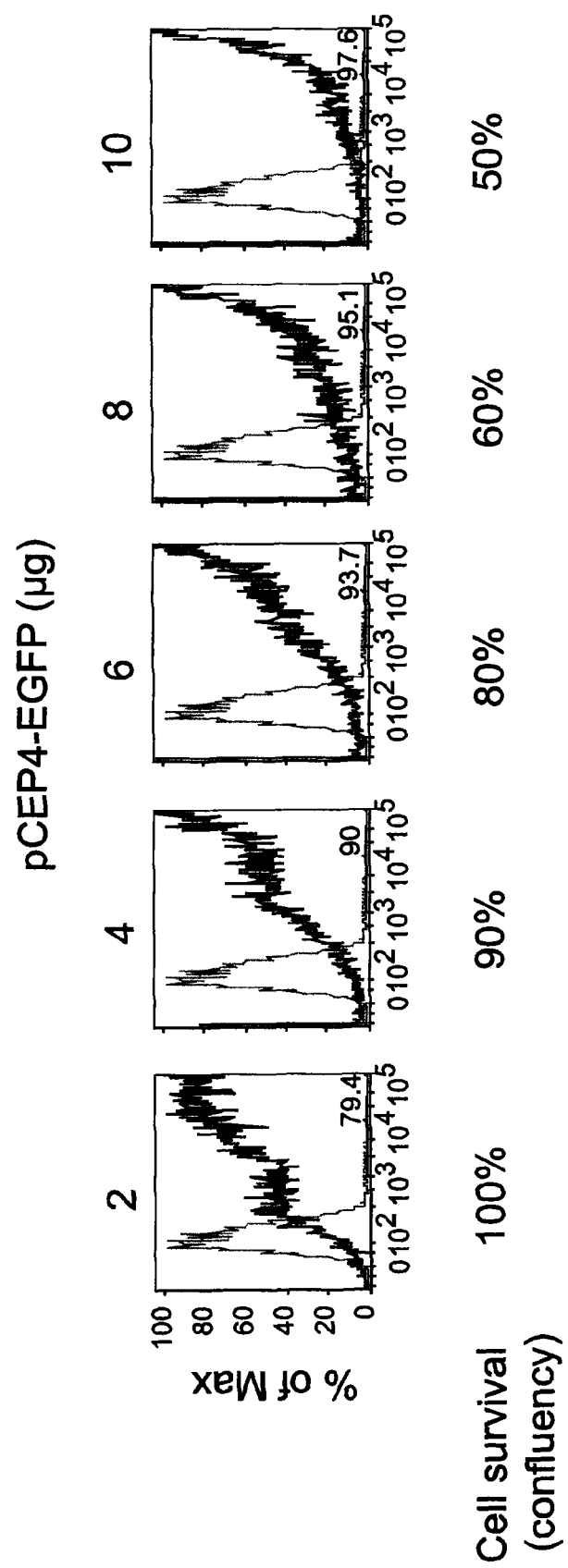

The present invention broadly relates to novel methods for reprogramming differentiated primate somatic cells into reprogrammed primate cells that are substantially free of the vectors used in their production by introducing potency-determining factors on a non-viral vector that is present during reprogramming, but is substantially absent from the reprogrammed cells. As used herein, "reprogramming" refers to a genetic process whereby differentiated somatic cells are converted into de-differentiated cells having a higher potency than the cells from which they were derived.

Advantageously, the higher potency cells produced in the method are euploid pluripotent cells. As used herein, "pluripotent cells" refer to a population of cells that express pluripotent cell-specific markers, have a cell morphology characteristic of undifferentiated cells (i.e., compact colony, high nucleus to cytoplasm ratio and prominent nucleolus) and can differentiate into all three germ layers (e.g., endoderm, mesoderm and ectoderm). When introduced into an immunocompromised animal, such as a SCID mouse, the pluripotent cells form teratomas that typically contain cells or tissues characteristic of all three germ layers. One of ordinary skill in the art can assess these characteristics by using techniques commonly used in the art. See, e.g., Thomson et al., supra. Pluripotent cells are capable of both proliferation in cell culture and differentiation towards a variety of lineage-restricted cell populations that exhibit multipotent properties. Pluripotent cells have a higher potency than somatic multipotent cells, which by comparison are more differentiated, but which are not terminally differentiated. The pluripotent products of primate somatic cell reprogramming methods are referred to herein as "reprogrammed primate pluripotent cells" or as induced pluripotent (iPS) cells. Such cells are suitable for use in research and therapeutic applications currently envisioned for human ES cells or existing iPS cells.

Differentiated somatic cells, including cells from a fetal, newborn, juvenile or adult primate, including human, individual, are suitable starting cells in the methods. Suitable somatic cells include, but are not limited to, bone marrow cells, epithelial cells, endothelial cells, fibroblast cells, hematopoietic cells, keratinocytes, hepatic cells, intestinal cells, mesenchymal cells, myeloid precursor cells and spleen cells. Another suitable somatic cell is a $CD29^+$ $CD44^+$ $CD166^+$ $CD105^+$ $CD73^+$ and $CD31^-$ mesenchymal cell that attaches to a substrate. Alternatively, the somatic cells can be cells that can themselves proliferate and differentiate into other types of cells, including blood stem cells, muscle/bone stem cells, brain stem cells and liver stem cells. Suitable somatic cells are receptive, or can be made receptive using methods generally known in the scientific literature, to uptake of potency-determining factors including genetic material encoding the factors. Uptake-enhancing methods can vary depending on the cell type and expression system. Exemplary conditions used to prepare receptive somatic cells having suitable transduction efficiency are well-known by those of ordinary skill in the art. The starting somatic cells can have a doubling time of about twenty-four hours.

The vectors described herein can be constructed and engineered using methods generally known in the scientific literature to increase their safety for use in therapy, to include selection and enrichment markers, if desired, and to optimize expression of nucleotide sequences contained thereon. The vectors should include structural components that permit the vector to self-replicate in the somatic starting cells. For example, the known Epstein Barr oriP/Nuclear Antigen-1 (EBNA-1) combination (see, e.g., Lindner, S. E. and B. Sugden, The plasmid replicon of Epstein-Barr virus: mechanistic insights into efficient, licensed, extrachromosomal replication in human cells, Plasmid 58:1 (2007), incorporated by reference as if set forth herein in its entirety) is sufficient to support vector self-replication and other combinations known to function in mammalian, particularly primate, cells can also be employed. Standard techniques for the construction of expression vectors suitable for use in the present invention are well-known to one of ordinary skill in the art and can be found in publications such as Sambrook J, et al., "Molecular cloning: a laboratory manual," (3rd ed. Cold Spring harbor Press, Cold Spring Harbor, N.Y. 2001), incorporated herein by reference as if set forth in its entirety.

In the methods, genetic material encoding a set of potency-determining factors is delivered into the somatic cells via one or more reprogramming vectors. Suitable potency-determining factors can include, but are not limited to OCT-4, SOX2, LIN28, NANOG, c-Myc, KLF4, and combinations thereof. Each potency-determining factor can be introduced into the somatic cells as a polynucleotide transgene that encodes the potency-determining factor operably linked to a heterologous promoter that can drive expression of the polynucleotide in the somatic cell. Although SV40 T Antigen is not a potency-determining factor per se, it advantageously introduced into somatic cells as it provides the cells with a condition sufficient to promote cell survival during reprogramming while the potency-determining factors are expressed. Other conditions sufficient for expression of the factors include cell culture conditions described in the examples.

Suitable reprogramming vectors are episomal vectors, such as plasmids, that do not encode all or part of a viral genome sufficient to give rise to an infectious or replication-competent virus, although the vectors can contain structural elements obtained from one or more virus. One or a plurality of reprogramming vectors can be introduced into a single somatic cell. One or more transgenes can be provided on a single reprogramming vector. One strong, constitutive transcriptional promoter can provide transcriptional control for a plurality of transgenes, which can be provided as an expression cassette. Separate expression cassettes on a vector can be under the transcriptional control of separate strong, constitutive promoters, which can be copies of the same promoter or can be distinct promoters. Various heterologous promoters are known in the art and can be used depending on factors such as the desired expression level of the potency-determining factor. It can be advantageous, as exemplified below, to control transcription of separate expression cassettes using distinct promoters having distinct strengths in the target somatic cells. Another consideration in selection of the transcriptional promoter(s) is the rate at which the promoter(s) is silenced in the target somatic cells. The skilled artisan will appreciate that it can be advantageous to reduce expression of one or more transgenes or transgene expression cassettes after the product of the gene(s) has completed or substantially completed its role in the reprogramming method. Exemplary promoters are the human EF1α elongation factor promoter, CMV cytomegalovirus immediate early promoter and CAG chicken albumin promoter, and corresponding homologous promoters from other species. In human somatic cells, both EF1α and CMV are strong promoters, but the CMV promoter is silenced more efficiently than the EF1α promoter such that expression of transgenes under control of the former is turned off sooner than that of transgenes under control of the latter.

The potency-determining factors can be expressed in the somatic cells in a relative ratio that can be varied to modulate reprogramming efficiency. For example, somatic cell reprogramming efficiency is fourfold higher when OCT-4 and SOX2 are encoded in a single transcript on a single vector in a 1:1 ratio than when the two factors are provided on separate vectors, such that the uptake ratio of the factors into single cells is uncontrolled. Preferably, where a plurality of transgenes is encoded on a single transcript, an internal ribosome entry site is provided upstream of transgene(s) distal from the transcriptional promoter. Although the relative ratio of factors can vary depending upon the factors delivered, one of ordinary skill in possession of this disclosure can determine an optimal ratio of factors.

The skilled artisan will appreciate that the advantageous efficiency of introducing all factors via a single vector rather than via a plurality of vectors, but that as total vector size increases, it becomes increasingly difficult to introduce the vector. The skilled artisan will also appreciate that position of a factor on a vector can affect its temporal expression, and the resulting reprogramming efficiency. As such, Applicants employed various combinations of factors on combinations of vectors. Several such combinations are here shown to support reprogramming.

After introduction of the reprogramming vector(s) and while the somatic cells are being reprogrammed, the vectors can persist in target cells while the introduced transgenes are transcribed and translated. Transgene expression can be advantageously downregulated or turned off in cells that have been reprogrammed to a pluripotent state. The reprogramming vector(s) can remain extra-chromosomal. At extremely low efficiency, the vector(s) can integrate into the cells' genome. The reprogramming vector(s) replicate coordinately with the recipient cell's genome and, as such, are reasonably stable for about two weeks, longer than episomal vectors that cannot replicate their DNA. Nevertheless, because the vectors are not partitioned evenly at cell division, in the absence of selective pressure, cells lose the episomal vector(s) so one can readily recover vector-free pluripotent cells in the method. For example, it usually takes two-to-three weeks for oriP/EBNA-1-based episomal plasmids to be stably maintained in somatic cells. During the initial two-to-three weeks, cells quickly lose episomal plasmids. Once the cells are stabilized, the cells continue to lose episomal vector at ~5% per generation.

Pluripotent cells produced in the method can be cultured in any medium that supports pluripotent cell growth, including but not limited to a defined medium, such as TeSR™ (StemCell Technologies, Inc.; Vancouver, Canada), mTeSR (StemCell Technologies, Inc.) and StemLine® serum-free medium (Sigma; St. Louis, Mo.), or a conditioned medium such as mouse embryonic fibroblast (MEF)-conditioned medium. As used herein, a "defined medium" refers to a biochemically defined formulation comprised solely of biochemically-defined constituents which can include constituents of known chemical composition or constituents derived from known sources. As used herein, "conditioned medium" refers to a growth medium that is further supplemented with soluble factors from cells cultured in the medium. Alternatively, cells can be maintained on MEFs in culture medium.

The invention will be more fully understood upon consideration of the following non-limiting Examples.

EXAMPLES

Example 1

Design and Construction of Expression Cassettes

Suitable expression cassettes structures were created using conventional methods by direct polymerase chain reaction (PCR) amplification of open reading frames (ORFs) from some or all of the transgenes, using the first and last 20-22 bases of the coding region as primers, and from the Internal Ribosome Entry Sites listed in Table 1. The sources of SV40 T Antigen and human telomerase reverse transcriptase, plasmids pBABE-puro SV40 LT and pBABE-hygro-hTERT, are commercially available from Addgene, Inc, Cambridge, Mass., as plasmids 13970 and 1773, respectively. The sources of IRES1 and IRES2, plasmids pIRESpuro3 and pIRES2EGFP, are commercially available from Clontech Laboratories, Inc., Mountain View, Calif. Foot-and-mouth disease virus segment 2, was chemically synthesized. In-frame expression cassettes are described using the codes set forth below in Table 1. For example, "E-O2S" refers to an expression cassette having an EF1α promoter upstream of the OCT4 and SOX2 coding regions, with IRES2 therebetween. Likewise, "C-M2K" refers to an expression cassette having a CMV promoter upstream of the c-Myc and Klf4 coding regions, with IRES2 therebetween. In several constructs, none of which was used in subsequent reprogramming, a variant O2S expression cassette ("O2S(2)") was employed that differed from O2S in that it contained a TK promoter-Hyg-TK polyA cassette (compare FIGS. 5A and 5B). Cassettes having the indicated structures were selected for subsequent use in reprogramming methods by empirical determination of expression levels of various factors. The promoter designated as EF2 (SEQ ID NO:12) was a slight variant from the known EF1α promoter (SEQ ID NO:11) that did not differ from EF1α in activity and which was not used in subsequent episomal vector reprogramming trials, infra. The F2A is a peptide linker that facilitates co-translation of distinct coding regions expressed from a single transcript. F2A was tested but was not used in subsequent reprogramming trials using episomal vectors. IRES1 was tested but was not used in subsequent reprogramming trials using episomal vectors.

The relative effects of various promoters, IRES sequences, and transgene arrangements on the expression of the upstream and downstream ORFs were evaluated by separately cloning various transgene expression cassettes into pSin4, a modified lentivirus-based vector, to test their ability to reprogram human somatic cells after transfection, as previously described (Yu et al., supra). 293FT cells were transfected with lentiviral plasmid vectors expressing OCT4 and SOX2 linked by IRES1 or IRES2 using SuperFect (Qiagen, Valencia, Calif.), as depicted below. Cells were collected two days post-transfection. FIG. 1A shows a Western blot analysis of OCT-4 and SOX2 in 293FT cells. Lane 1, pSIN4-EF2-OCT4-IRES1-SOX2; lane 2, pSIN4-EF2-OCT4-IRES2-SOX2; lane 3, pSIN4-EF2-OCT4-F2A-SOX2; lane 4, pSIN4-EF2-OCT4-IRES1-PURO; lane 5, pSIN4-EF2-SOX2-IRES1-PURO; lane 6, no plasmid (control). Mouse anti-human OCT4 monoclonal antibody (1:500, Santa Cruz Biotechnology, Inc., Santa Cruz, Calif., sc-5279) and goat anti-human SOX2 polyclonal antibody (1:500, R&D Systems, Minneapolis, Minn. AF2018) were used to detect the relative expression of OCT4 and SOX2 respectively.

FIG. 1B shows reprogramming using linked potency-determining factors in $0.2 \times 10^6$ mesenchymal cells derived (Yu et al., supra) from OCT4 knock-in human ES cells (US Patent Application No. 2006/0128018 and Zwaka and Thomson, Nature Biotechnology 21:319-321 (2003), each incorporated herein by reference as if set forth in its entirety). This line was maintained under neomycin selection (geneticin: 100 µg/ml, Invitrogen Corp.). Human iPS cell colonies were counted on day 16 post-transduction. The gene combinations were pSIN4-EF2-OCT4-IRES1-SOX2 (O1S); pSIN4-EF2-OCT4-IRES2-SOX2 (O2S); pSIN4-EF2-OCT4-F2A-SOX2 (OF2AS); pSIN4-EF2-NANOG-IRES1-LIN28 (N1L); pSIN4-EF2-NANOG-IRES2-LIN28 (N2L); pSIN4-EF2-OCT4-IRES1-PURO (O); pSIN4-EF2-SOX2-IRES1-PURO (S); pSIN4-EF2-NANOG-IRES1-PURO (N); pSIN4-EF2-LIN28-IRES1-PURO (L). The abbreviation used for each lentiviral plasmid vector is shown in parentheses after the vector name.

Example 2

Reprogramming Human Newborn Foreskin Fibroblasts Using Lentiviral Constructs

Preliminary reprogramming experiments were conducted by introducing lentiviral vectors into human neonatal foreskin fibroblasts. FIG. 2A shows that NANOG has a profound positive effect on reprogramming efficiency when OCT4, SOX2, LIN28, and c-MYC are also introduced, and that in combination with OCT4, SOX2, and LIN28, NANOG can support reprogramming, even in the absence of c-MYC or KLF4. Lentiviral constructs used were pSIN4-EF2-OCT4-IRES2-SOX2 (O2S); pSIN4-EF2-NANOG-IRES2-LIN28 (N2L); pSIN4-EF2-LIN28-IRES1-PURO (L); pSIN4-CMV-c-Myc-IRES1-PURO (M); pSIN4-EF2-KLF4-IRES1-PURO (K). Twenty-one days after transduction, alkaline phosphatase-positive human iPS cell colonies were counted. The number of iPS cell colonies were derived from an input of $2.5 \times 10^4$ human newborn foreskin fibroblasts (passage 9). The light gray bars represent the total number of reprogrammed colonies formed having typical human ES cell morphology; dark gray bars indicate the number of large colonies with minimal differentiation.

FIG. 2B evidences reprogramming using linked potency-determining factors. Lentiviral constructs used were pSIN4-EF2-c-Myc-IRES2-KLF4 (EF2-M2K); pSIN4-CMV-c-Myc-IRES2-KLF4 (CMV-M2K); pSIN4-EF2-KLF4-IRES2-c-Myc (EF2-K2M); pSIN4-CMV-KLF4-IRES2-c-Myc (CMV-K2M); pSIN4-CMV-c-Myc-IRES2-LIN28 (M2L); pSIN4-EF2-NANOG-IRES2-KLF4 (N2K). Fourteen days after transduction, alkaline phosphatase-positive human iPS cell colonies were counted. The number of iPS cell colonies were derived from an input of approximately $7.0 \times 10^4$ foreskin fibroblasts (passage 12). The asterisk indicates that most of the alkaline phosphatase-positive colonies appeared morphologically loose.

FIG. 2C shows the effect of SV40 large T antigen gene expression on reprogramming efficiency. SV40 large T antigen prevents c-Myc-induced in murine fibroblasts (Hermeking et al., PNAS 91:10412-10416 (1994)) and enhances reprogramming efficiency (Hanna et al., Cell 133:250-264 (2008); Mali et al., Stem Cells doi: 10.1634/stemcells. 2008-0346 (2008)). Abbreviations of gene combinations are the same as in FIG. 2B, with the addition of SV40 large T antigen (T). c-Myc also promotes cell proliferation. Twelve days after transduction, alkaline phosphatase-positive human iPS cell colonies were counted. The number of iPS cell colonies were derived from an input of approximately $\sim 3.5 \times 10^4$ foreskin fibroblasts (passage 17). FIG. 2C demonstrates that if present at levels achieved during lentiviral-based reprogramming, T antigen inhibits final stages of iPS cell derivation. In contrast, see infra, wherein T antigen does not have this effect when present for the temporal expression time and/or level achieved during reprogramming using episomal vectors. In addition, T antigen prevents c-Myc-induced apoptosis but does not adversely affect c-Myc-induced cell proliferation.

Example 3

Reprogramming of Human Newborn Foreskin Fibroblasts Using Non-viral Episomal Constructs Human newborn foreskin fibroblasts (Cat# CRL-2097™, ATCC) were maintained in foreskin fibroblast culture medium (DMEM (Cat#11965, Invitrogen) supplemented with 10% heat-inactivated fetal bovine serum (FBS, HyClone Laboratories, Logan, Utah), 2 mM Glutamax, 0.1 mM non-essential amino acids, and 0.1 mM β-mercaptoethanol).

Various combinations of potency-determining factors provided as transgene expression cassettes constructed as in Example 1 and as detailed below in Table 3 were introduced into somatic cells using an episomal construct pCEP4-EGFP (as shown in FIG. 3A) resulting in reprogramming with varying efficiency. pCEP4-EGFP was created from commercially available mammalian episomal expression vector pCEP4 (Invitrogen Corp., Carlsbad, Calif.) by inserting the EGFP coding region between the pCEP4 BamHI and NheI sites. The episomal vectors of Table 2 were created by inserting the designated expression cassettes into pCEP4-EGFP or into a related backbone lacking $P_{CMV}$ (designated pEP4). See FIG. 3A and Table 2 footnotes for cloning sites into which expression cassettes were inserted.

Vectors were introduced into the fibroblasts via a single nucleofection event, using Human Dermal Fibroblasts Nucleofector Kit (Normal Human Dermal Fibroblasts, Amaxa, Inc. Cat. No. VPD-1001), in accord with the manufacturer's instructions. After nucleofection, the transfected fibroblasts (~0.8 to 1.0×10$^6$ cells each) were immediately plated onto three 10 cm dishes seeded with irradiated mouse embryonic fibroblasts (MEF). Foreskin fibroblast culture medium was replaced every other day. After four days, the foreskin fibroblast culture medium was replaced with human ES cell culture medium (DMEM/F12 culture medium supplemented with 20% KnockOut serum replacer, 0.1 mM non-essential amino acids (all from Invitrogen Corp.), 1 mM Glutamax, 0.1 mM β-mercaptoethanol and 100 ng/ml zebrafish basic fibroblast growth factor (zbFGF) as previously described (Amit et al., Developmental Biology 227: 271-278 (2006); Ludwig et al., Nature Methods 3:637-646 (2006), each of which is incorporated herein by reference as if set forth in its entirety). When the seeded MEF could no longer sustain the reprogramming culture, about 8 to 10 days after plating, human ES cell culture medium conditioned with irradiated MEF was used instead. When appropriate (about 2-3 weeks after transfection), the cultures were stained for alkaline phosphatase as an indication of human iPS colony development.

To determine suitable parameters for introducing transgene constructs, temporal expression was initially evaluated by measuring EGFP level over time after introduction of EGFP from pEGFP-N2 (control) and pCEP4-EGFP episomal vector into 293FT cells was evaluated (FIG. 3B).

The effect of the amount of transgene construct introduced on human newborn foreskin fibroblast cell survival was also evaluated in preliminary experiments. FIG. 3C shows the effect of amount of pCEP4-EGFP episomal vector used on nucleofection efficiency and survival of human newborn foreskin fibroblasts, estimated from cell confluence on the day after nucleofection. Approximately 1×10$^6$ nucleofected foreskin fibroblasts were plated into each well of a 6-well plate. Gray lines represent non-transfected control fibroblasts; black lines represent transfected fibroblasts.

FIG. 4A depicts schematic transgene expression constructs from Table 3 containing various expression cassettes that when introduced in certain combinations into human newborn foreskin fibroblasts result in reprogramming of the fibroblasts to pluripotent cells. Three combinations of introduced episomal reprogramming vectors have yielded reprogrammed pluripotent cells: (1) pEP4-E-O2S-E-T2K, pEP4-E-O2S-E-N2K and pCEP4-C-M2L; (2) pEP4-E-O2S-C-K2M-E-N2L and pEP4-E-O2S-E-T2K; and (3) pEP4-E-O2S-E-N2L, pEP4-E-O2S-E-T2K and pEP4-E-O2S-E-M2K. Table 3 indicates the amount of each vector used in each successful combination. One vector in each successful reprogramming combination encoded T antigen under control of the EF1α promoter.

FIG. 4B shows a bright-field microscopy image of a typical colony with morphological changes observed 18 days after episomal vector transfection. FIG. 4C shows a bright-field microscopy image of an alkaline phosphatase-positive colony 18 days after episomal vector transfection.

Twenty-five to thirty days after transfection, the reprogramming cultures were passaged once to fresh 10 cm MEF dishes (1:3 ratio), due to the presence of many non-iPS cell colonies with morphologies similar to human iPS cell colonies. Colonies were then picked for further analysis. FIG. 4D shows a bright-field microscopy image of a human iPS cell colony 6 days after the first passage of day 28 post-transfection reprogramming culture. The scale bar represents 0.1 mm.

Reprogrammed cells were maintained for subsequent analysis in feeder-free culture on Matrigel (BD Biosciences, Bedford, Mass.) with conditioned medium as previously described (Xu et al., Nat. Biotechnol. 19:971 (2001), incorporated herein by reference as if set forth in its entirety).

Advantageously, the reprogramming efficiency of greater than 1% of the newborn foreskin fibroblast cells reprogrammed was achieved, at significantly lower reprogramming time than was achieved using four gene combinations.

It is understood that certain adaptations of the invention described in this disclosure are a matter of routine optimization for those skilled in the art, and can be implemented without departing from the spirit of the invention, or the scope of the appended claims. All publications and patents mentioned in the above specification are herein incorporated by reference. Various modifications and variations of the described method and system of the invention will be apparent to those skilled in the art without departing from the scope and spirit of the invention. It is understood, however, that examples and embodiments of the present invention set forth above are illustrative and not intended to confine the invention. The invention embraces all modified forms of the examples and embodiments as come with the scope of the following claims.

TABLE 1

Reprogramming genes and translation elements

| Gene Symbol | Abbr. | Source | SEQ ID NO | Accession # or sequence |
|---|---|---|---|---|
| OCT4 | O | hESC | 1 | NM_002701 |
| SOX2 | S | hESC | 2 | NM_003106 |
| NANOG | N | hESC | 3 | NM_024865 |
| LIN28 | L | hESC | 4 | NM_024674 |
| c-Myc | M | hESC | 5 | NM_002467 |
| KLF4 | K | hESC | 6 | NM_004235 |
| SV40 T | T | pBABE-puro SV40 LT p | 7 | EF579667 |
| TERT | TERT | pBABE-hygro-hTERT | 8 | NM_198253 |
| IRES1 | 1 | pIRESpuro3 | — | |
| IRES2 | 2 | pIRES2EGFP | — | |
| F2A | F2A | (synthesized) | 9 | |
| CMV | C | | 10 | |
| EF1α | E | | 11 | |
| EF2α | — | | 12 | |

TABLE 2

Episomal constructs

| # | Name | Size (bp) |
|---|---|---|
| 1 | pCEP4-EGFP | 10984 |
| 2$^b$ | pEP4-E-O2S(2) | 13523 |
| 3$^b$ | pEP4-E-M2K | 14293 |
| 4$^a$ | pCEP4-M2K | 13643 |
| 5$^b$ | pEP4-E-K2M | 14268 |
| 6$^a$ | pCEP4-K2M | 13636 |
| 7$^b$ | pEP4-E-N2K | 13819 |
| 8$^b$ | pEP4-E-T2K | 15071 |
| 9$^a$ | pCEP4-M2L | 12852 |
| 10$^b$ | pEP4-E-N2L | 13020 |
| 11$^b$ | pEP4-E-T2L | 14284 |
| 12$^c$ | pEP4-E-O2S-C-M2K | 16038 |
| 13$^c$ | pEP4-E-O2S-E-M2K | 16680 |
| 14$^c$ | pEP4-E-O2S-C-K2M | 16010 |
| 15$^c$ | pEP4-E-O2S-E-K2M | 16652 |
| 16$^c$ | pEP4-E-O2S-E-N2K | 16206 |
| 17$^c$ | pEP4-E-O2S-E-T2K | 17458 |
| 18$^c$ | pEP4-E-O2S-E-N2L | 15415 |

TABLE 2-continued

Episomal constructs

| # | Name | Size (bp) |
|---|------|-----------|
| 19[c] | pEP4-E-O2S-E-T2L | 16679 |
| 20[c] | pEP4-O2S-C-M2L | 15247 |
| 21[c] | pEP4-E-O2S-E-K2T | 17474 |
| 22[c] | pEP4-E-O2S-C-M2L-E-N2K | 19956 |
| 23[c] | pEP4-E-O2S-C-M2K-E-N2L | 19956 |
| 24[c] | pEP4-E-O2S-C-K2M-E-N2L | 19949 |
| 25[c] | pEP4-E-O2S-C-M2L-E-T2K | 21220 |
| 26[c] | pEP4-E-O2S-C-M2K-E-T2L | 21220 |
| 27[c] | pEP4-E-O2S-C-K2M-E-T2L | 21213 |
| 28[c] | pEP4-E-O2S-C-M2L-E-K2T | 21224 |

[a]All linked gene cassettes were cloned into the pCEP4-EGFP between BamHI and NheI restriction sites.
[b]All linked gene cassettes plus the EF1α promoter were cloned into the pCEP4-EGFP between BamHI and SpeI (19) restriction sites.
[c]All expression cassettes were cloned into the pCEP4-EGFP between BamHI and NruI restriction sites.

TABLE 3

Combinations of episomal constructs tested for reprogramming activity

| Equivalent of pCEP4-EGF (μg) | Test # | Plasmids | μg | Morph. Changes | AP+ colony/plate |
|---|---|---|---|---|---|
| EXPERIMENT 1 | | | | | |
| 6.3 | 1 | pEP4-E-O2S-C-M2K | 9.2 | +/− | 0 |
| 6.3 | 2 | pEP4-E-O2S-K2Neo | 9.3 | +/− | 0 |
| 6.3 | | pCEP4-M2L | 7.4 | | |
| 6.3 | 3 | pEP4-E-O2S-E-N2K | 9.3 | +/− | 0 |
| 6.3 | | pCEP4-M2L | 7.4 | | |
| 6.3 | 4 | pEP4-E-O2S-E-T2K | 10 | +++ | 0 |
| 6.3 | | pCEP4-M2L | 7.4 | | |
| 6.3 | 5 | pEP4-E-O2S-E-TERT2K | 10.8 | +/− | 0 |
| 6.3 | | pCEP4-M2L | 7.4 | | |
| 6.3 | 6 | pEP4-E-O2S-C-M2L | 8.7 | +/− | 0 |
| 6.3 | | pEP4-E-N2K | 7.9 | | |
| 6.3 | 7 | pEP4-E-O2S-C-M2L | 8.7 | + | 0 |
| 6.3 | | pEP4-E-T2K | 8.6 | | |
| 6.3 | 8 | pEP4-E-O2S-C-M2L | 8.7 | +/− | 0 |
| 6.3 | | pEP4-E-TERT2K | 9.4 | | |
| EXPERIMENT 2 | | | | | |
| 3.3 | 1 | pEP4-E-O2S-C-M2K | 5.0 | +/− | 0 |
| 3.3 | 2 | pEP4-E-O2S-E-M2K | 5.0 | +/− | 0 |
| 3.3 | 3 | pEP4-E-O2S-C-K2M | 5.0 | +/− | 0 |
| 3.3 | 4 | pEP4-E-O2S-E-K2M | 5.0 | +/− | 0 |
| 2.5 | 5 | pEP4-E-O2S(2) | 3.0 | +/− | 0 |
| 2.5 | | pCEP4-M2K | 3.0 | | |
| 2.5 | 6 | pEP4-E-O2S(2) | 3.0 | +/− | 0 |
| 2.3 | | pEP4-E-M2K | 3.0 | | |
| 2.5 | 7 | pEP4-E-O2S(2) | 3.0 | +/− | 0 |
| 2.5 | | pCEP4-K2M | 3.0 | | |
| 2.5 | 8 | pEP4-E-O2S(2) | 3.0 | +/− | 0 |
| 2.3 | | pEP4-E-K2M | 3.0 | | |
| 1.7 | 9N | pEP4-E-O2S(2) | 2.0 | +/− | 0 |
| 1.5 | | pEP4-E-N2K | 2.0 | | |
| 1.7 | | pCEP4-M2L | 2.0 | | |
| 1.7 | 10N | pEP4-E-O2S(2) | 2.0 | +/− | 0 |
| 1.7 | | pEP4-E-N2L | 2.0 | | |
| 1.7 | | pCEP4-M2K | 2.0 | | |
| 1.7 | 11N | pEP4-E-O2S(2) | 2.0 | +/− | 0 |
| 1.7 | | pEP4-E-N2L | 2.0 | | |
| 1.5 | | pEP4-E-M2K | 2.0 | | |
| 1.7 | 12N | pEP4-E-O2S(2) | 2.0 | +/− | 0 |
| 1.7 | | pEP4-E-N2L | 2.0 | | |
| 1.7 | | pCEP4-K2M | 2.0 | | |
| 1.7 | 13N | pEP4-E-O2S(2) | 2.0 | +/− | 0 |
| 1.7 | | pEP4-E-N2L | 2.0 | | |
| 1.5 | | pEP4-E-K2M | 2.0 | | |
| 2.3 | 14N | pEP4-E-O2S-E-N2K | 3.5 | +/− | 0 |
| 2.1 | | pCEP4-M2L | 2.5 | | |
| 2.5 | 15N | pEP4-E-O2S-E-N2L | 3.5 | +/− | 0 |
| 2.1 | | pCEP4-M2K | 2.5 | | |
| 2.5 | 16N | pEP4-E-O2S-E-N2L | 3.5 | +/− | 0 |
| 1.9 | | pEP4-E-M2K | 2.5 | | |
| 2.5 | 17N | pEP4-E-O2S-E-N2L | 3.5 | +/− | 0 |
| 2.1 | | pCEP4-K2M | 2.5 | | |
| 2.5 | 18N | pEP4-E-O2S-E-N2L | 3.5 | +/− | 0 |
| 1.9 | | pEP4-E-K2M | 2.5 | | |

TABLE 3-continued

Combinations of episomal constructs tested for reprogramming activity

| Equivalent of pCEP4-EGF (µg) | Test # | Plasmids | µg | Morph. Changes | AP+ colony/ plate |
|---|---|---|---|---|---|
| | EXPERIMENT 3 ||||||

| Equivalent of pCEP4-EGF (µg) | Test # | Plasmids | µg | Morph. Changes | AP+ colony/ plate |
|---|---|---|---|---|---|
| 1.7 | 9T | pEP4-E-O2S(2) | 2.0 | ++ | 0 |
| 1.4 | | pEP4-E-T2K | 2.0 | | |
| 1.7 | | pCEP4-M2L | 2.0 | | |
| 1.7 | 10T | pEP4-E-O2S(2) | 2.0 | + | 0 |
| 1.5 | | pEP4-E-T2L | 2.0 | | |
| 1.7 | | pCEP4-M2K | 2.0 | | |
| 1.7 | 11T | pEP4-E-O2S(2) | 2.0 | + | 0 |
| 1.5 | | pEP4-E-T2L | 2.0 | | |
| 1.5 | | pEP4-E-M2K | 2.0 | | |
| 1.7 | 12T | pEP4-E-O2S(2) | 2.0 | +/− | 0 |
| 1.5 | | pEP4-E-T2L | 2.0 | | |
| 1.7 | | pCEP4-K2M | 2.0 | | |
| 1.7 | 13T | pEP4-E-O2S(2) | 2.0 | +/− | 0 |
| 1.5 | | pEP4-E-T2L | 2.0 | | |
| 1.5 | | pEP4-E-K2M | 2.0 | | |
| 2.2 | 14T | pEP4-E-O2SET2K | 3.5 | +++ | 0 |
| 2.1 | | pCEP4-M2L | 2.5 | | |
| 2.3 | 15T | pEP4-E-O2S-E-T2L | 3.5 | + | 0 |
| 2.1 | | pCEP4-M2K | 2.5 | | |
| 2.3 | 16T | pEP4-E-O2S-E-T2L | 3.5 | + | 0 |
| 1.9 | | pEP4-E-M2K | 2.5 | | |
| 2.3 | 17T | pEP4-E-O2S-E-T2L | 3.5 | +/− | 0 |
| 2.1 | | pCEP4-K2M | 2.5 | | |
| 2.3 | 18T | pEP4-E-O2S-E-T2L | 3.5 | +/− | 0 |
| 1.9 | | pEP4-E-K2M | 2.5 | | |
| 1.9 | 19 | pEP4-E-O2S-E-T2K | 3.0 | +++ | 1 |
| 2.0 | | pEP4-E-O2S-E-N2K | 3.0 | | |
| 1.7 | | pCEP4-M2L | 2.0 | | |
| | EXPERIMENT 4 ||||||
| 6 | 1 | pEP4-E-O2S-C-M2K-E-N2L | 10.9 | +/− | 0 |
| 4 | 2 | pEP4-E-O2S-C-M2K-E-N2L | 7.3 | +++ | 0 |
| 2 | | pEP4-E-O2S-E-T2K | 3.2 | | |
| 6 | 3 | pEP4-E-O2S-C-K2M-E-N2L | 10.9 | +/− | 0 |
| 4 | 4 | pEP4-E-O2S-C-K2M-E-N2L | 7.3 | ++ | 2 |
| 2 | | pEP4-E-O2S-E-T2K | 3.2 | | |
| 3 | 5 | pEP4-E-O2S-E-N2L | 4.2 | +/− | 0 |
| 3 | | pEP4-E-O2S-E-M2K | 4.6 | | |
| 3 | 6 | pEP4-E-O2S-E-N2L | 4.2 | ++ | 1 |
| 2 | | pEP4-E-O2S-E-T2K | 3.2 | | |
| 3 | | pEP4-E-O2S-E-M2K | 4.6 | | |
| 3 | 7 | pEP4-E-O2S-E-N2L | 4.2 | +/− | 0 |
| 3 | | pEP4-E-O2S-C-M2K | 4.4 | | |
| 3 | 8 | pEP4-E-O2S-E-N2L | 4.2 | + | 0 |
| 2 | | pEP4-E-O2S-E-T2K | 3.2 | | |
| 3 | | pEP4-E-O2S-C-M2K | 4.4 | | |
| 3 | 9 | pEP4-E-O2S-E-N2L | 4.2 | +/− | 0 |
| 3 | | pEP4-E-O2S-E-K2M | 4.5 | | |
| 3 | 10 | pEP4-E-O2S-E-N2L | 4.2 | +/− | 0 |
| 2 | | pEP4-E-O2S-E-T2K | 3.2 | | |
| 3 | | pEP4-E-O2S-E-K2M | 4.5 | | |
| 3 | 11 | pEP4-E-O2S-E-N2L | 4.2 | +/− | 0 |
| 3 | | pEP4-E-O2S-C-K2M | 4.4 | | |
| 3 | 12 | pEP4-E-O2S-E-N2L | 4.2 | + | 0 |
| 2 | | pEP4-E-O2S-E-T2K | 3.2 | | |
| 3 | | pEP4-E-O2S-C-K2M | 4.4 | | |
| 2 | 13 | pEP4-E-O2S-C-M2L-E-T2K | 3.9 | + | 0 |
| 4 | | pEP4-E-O2S-E-N2K | 5.9 | | |
| 6 | 14 | pEP4-E-O2S-C-M2K-E-T2L | 11.6 | + | 0 |
| 3 | 15 | pEP4-E-O2S-C-M2K-E-T2L | 5.8 | + | 0 |
| 3 | | pEP4-E-O2S-E-N2K | 4.4 | | |
| 6 | 16 | pEP4-E-O2S-C-K2M-E-T2L | 11.6 | +/− | 0 |
| 3 | 17 | pEP4-E-O2S-C-K2M-E-T2L | 5.8 | + | 0 |
| 3 | | pEP4-E-O2S-E-N2K | 4.4 | | |

TABLE 3-continued

Combinations of episomal constructs tested for reprogramming activity

| Equivalent of pCEP4-EGF (μg) | Test # | Plasmids | μg | Morph. Changes | AP+ colony/plate |
|---|---|---|---|---|---|
| 6 | 18 | pEP4-E-O2S-C-M2L-E-K2T | 11.6 | +/− | 0 |
| 3 | 19 | pEP4-E-O2S-C-M2L-E-K2T | 5.8 | +/− | 0 |
| 3 |  | pEP4-E-O2S-E-N2K | 4.4 |  |  |
| 3 | 20 | pEP4-E-O2S-E-K2T | 4.8 | +/− | 0 |
| 3 |  | pEP4-E-O2S-E-N2K | 4.4 |  |  |
| 2 |  | pEP4-E-O2S-C-M2L | 2.8 |  |  |

+/−: No or very few colonies with morphological change were observed (FIG. 4B).
+, ++ and +++: Different number (from less to more) of colonies with morphological change were observed.

---

We claim:

1. A method of reprogramming primate somatic cells, the method comprising the steps of:
   introducing into a primate somatic cell at least one non-viral episomal vector that encodes at least one potency-determining factor under conditions sufficient to reprogram the cells, wherein the at least one vector encodes at least potency-determining factors OCT4 and SOX2, wherein the cells express the introduced OCT4 and SOX2 and further comprise SV40 T Antigen; and
   culturing the cells obtained from the introducing step in a medium that supports pluripotent cell growth to obtain pluripotent reprogrammed cells substantially free of any vector component associated with introducing the potency-determining factors to the somatic cells.

2. The method of claim 1, wherein the primate somatic cells are obtained from a fetal or post-natal primate individual.

3. The method of claim 1, wherein the primate is a human.

4. The method of claim 1, wherein the reprogrammed cells are genetically identical to a fetal or post-natal individual.

5. The method of claim 1, wherein at least one vector further encodes at least one potency-determining factor selected from the group consisting of LIN28, NANOG, c-Myc, and KLF4.

6. The method of claim 1, wherein a single vector encodes at least OCT4 and SOX2 and comprises at least one operably positioned internal ribosomal entry site.

7. The method of claim 6, wherein the single vector comprises, in order, a first promoter, OCT4, IRES2, SOX2, a second promoter, SV40 T antigen, IRES2, and KLF4.

8. The method of claim 6, wherein the vector comprises, in order, a first promoter, OCT4, IRES2, SOX2, a second promoter, c-Myc, IRES 2, KLF4, a third promoter, NANOG, IRES2, and LIN28.

9. The method of claim 1, wherein a first vector comprises, in order, a first promoter, OCT4, IRES2, SOX2, a second promoter, SV40 T antigen, IRES2, and KLF4, wherein a second vector comprises, in order, a third promoter, OCT4, IRES2, SOX2, a fourth promoter, NANOG, IRES2, and KLF4, and wherein a third vector comprises, in order, a fifth promoter, c-Myc, IRES 2, and LIN28, wherein the promoters need not be identical.

10. The method of claim 9, wherein each of the first, second, third, and fourth promoters is an elongation factor 1α (EF1α) gene promoter.

11. The method of claim 1, wherein a first vector comprises, in order, a first promoter, OCT4, IRES2, SOX2, a second promoter, KLF4, IRES2, c-Myc, a third promoter, NANOG, IRES2, and LIN28, wherein a second vector comprises, in order, a fourth promoter, OCT4, IRES2, SOX2, a fifth promoter, SV40 T antigen, IRES2, and KLF4, wherein the promoters need not be identical.

12. The method of claim 11, wherein each of the first, third, fourth, and fifth promoters is an EF1α gene promoter and wherein the second promoter is a cytomegalovirus immediate early gene (CMV) promoter.

13. The method of claim 1, wherein a first vector comprises, in order, a first promoter, OCT4, IRES2, SOX2, a second promoter, NANOG, IRES2, and LIN28, wherein a second vector comprises, in order, a third promoter, OCT4, IRES2, SOX2, a fourth promoter, SV40 T antigen, IRES2, and KLF4, and wherein a third vector comprises, in order, a fifth promoter, OCT4, IRES2, SOX2, a sixth promoter, c-Myc, IRES 2, and KLF4, wherein the promoters need not be identical.

14. The method of claim 1, wherein at least one vector encodes a plurality of factors and at least one vector comprises at least one internal ribosomal entry site.

15. The method of claim 1, wherein OCT4 and SOX2 are human.

16. The method of claim 1, wherein LIN28, NANOG, c-Myc, and KLF4 are human.

* * * * *

(12) EX PARTE REEXAMINATION CERTIFICATE (10634th)
United States Patent
Thomson et al.

(10) Number: US 8,268,620 C1
(45) Certificate Issued: Jun. 19, 2015

(54) OCT4 AND SOX2 WITH SV40 T ANTIGEN PRODUCE PLURIPOTENT STEM CELLS FROM PRIMATE SOMATIC CELLS

(75) Inventors: James Thomson, Madison, WI (US); Junying Yu, Middleton, WI (US)

(73) Assignee: WISCONSIN ALUMNI RESEARCH FOUNDATION, Madison, WI (US)

Reexamination Request:
No. 90/020,068, Apr. 25, 2014

Reexamination Certificate for:
Patent No.: 8,268,620
Issued: Sep. 18, 2012
Appl. No.: 12/605,220
Filed: Oct. 23, 2009

Related U.S. Application Data

(60) Provisional application No. 61/108,362, filed on Oct. 24, 2008.

(51) Int. Cl.
*C12N 15/00* (2006.01)
*C12N 5/074* (2010.01)
*C12N 15/85* (2006.01)

(52) U.S. Cl.
CPC ........ *C12N 5/0696* (2013.01); *C12N 2501/608* (2013.01); *C12N 15/85* (2013.01); *C12N 2510/00* (2013.01); *C12N 2501/602* (2013.01); *C12N 2501/605* (2013.01); *C12N 2501/606* (2013.01); *C12N 2501/604* (2013.01); *C12N 2501/603* (2013.01)

(58) Field of Classification Search
None
See application file for complete search history.

(56) References Cited

To view the complete listing of prior art documents cited during the proceeding for Reexamination Control Number 90/020,068, please refer to the USPTO's public Patent Application Information Retrieval (PAIR) system under the Display References tab.

*Primary Examiner* — Bruce Campell

(57) ABSTRACT

Methods for reprogramming primate somatic cells to pluripotency using an episomal vector that does not encode an infectious virus are disclosed. Pluripotent cells produced in the methods are also disclosed.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-16 is confirmed.

\* \* \* \* \*